United States Patent
Kumar et al.

(10) Patent No.: US 10,251,705 B2
(45) Date of Patent: Apr. 9, 2019

(54) SOFTWARE FOR USE WITH DEFORMITY CORRECTION

(71) Applicant: Stryker European Holdings I, LLC, Kalamazoo, MI (US)

(72) Inventors: Anup Kumar, Gurgaon (IN); Sridhar Anjanappa, Gurgaon (IN); Ashish Gangwar, Gurgaon (IN); Manash Lahiri, Gurgaon (IN); Arpit Gautam, Gurgaon (IN); Kanishk Sethi, Gurgaon (IN); Sistu Ganesh, Gurgaon (IN)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 15/171,121

(22) Filed: Jun. 2, 2016

(65) Prior Publication Data

US 2017/0348054 A1 Dec. 7, 2017

(51) Int. Cl.
*G06K 9/00* (2006.01)
*A61B 34/10* (2016.01)
(Continued)

(52) U.S. Cl.
CPC .............. *A61B 34/10* (2016.02); *A61B 34/25* (2016.02); *A61B 17/62* (2013.01);
(Continued)

(58) Field of Classification Search
USPC ....................................................... 382/128
See application file for complete search history.

(56) References Cited

U.S. PATENT DOCUMENTS 5,546,942 A 8/1996 Zhang
5,681,309 A 10/1997 Ross, Jr. et al.
(Continued)

FOREIGN PATENT DOCUMENTS

DE 102006048451 A1 4/2008
EP 2767252 A1 * 8/2014 ............. A61B 19/00
(Continued)

OTHER PUBLICATIONS

Extended European Seach Report for Application No. 14154820.6 dated Jun. 16, 2014.
(Continued)

*Primary Examiner* — Gregory F Cunningham
(74) *Attorney, Agent, or Firm* — Lerner, David, Littenberg, Krumholz & Mentlik, LLP

(57) ABSTRACT

A method of generating a correction plan for correcting a deformed bone includes inputting to a computer system a first image of the deformed bone in a first plane and inputting to the computer system a second image of the deformed bone in a second plane. Image processing techniques are employed to identify a plurality of anatomical landmarks of the deformed bone in the first image. The first image of the deformed bone is displayed on a display device. A graphical of the deformed bone is autonomously generated and graphically overlaid on the first image of the deformed bone on the display device, the graphical template including a plurality of lines, each line connected at each end to a landmark point corresponding to one of the anatomical landmarks. A model of the deformed bone may be autonomously generated based on the graphical template.

21 Claims, 19 Drawing Sheets

(51) Int. Cl.
*A61B 34/00* (2016.01)
*A61B 17/62* (2006.01)
*A61B 90/00* (2016.01)

(52) U.S. Cl.
CPC ... *A61B 2034/104* (2016.02); *A61B 2034/105* (2016.02); *A61B 2034/107* (2016.02); *A61B 2034/108* (2016.02); *A61B 2090/376* (2016.02)

(56) References Cited

U.S. PATENT DOCUMENTS

| | | | |
|---|---|---|---|
| 5,682,886 | A | 11/1997 | Delp et al. |
| 5,702,389 | A | 12/1997 | Taylor et al. |
| 5,728,095 | A | 3/1998 | Taylor et al. |
| 5,769,092 | A | 6/1998 | Williamson, Jr. |
| 5,824,085 | A | 10/1998 | Sahay et al. |
| 5,880,976 | A | 3/1999 | DiGioia, III et al. |
| 5,891,143 | A | 4/1999 | Taylor et al. |
| 5,971,984 | A | 10/1999 | Taylor et al. |
| 6,030,386 | A | 2/2000 | Taylor et al. |
| 6,112,109 | A | 8/2000 | D'Urso |
| 6,129,727 | A | 10/2000 | Austin et al. |
| 6,205,411 | B1 | 3/2001 | DiGioia, III et al. |
| 6,701,174 | B1 | 3/2004 | Krause et al. |
| 6,711,432 | B1 | 3/2004 | Krause et al. |
| 7,039,225 | B2 | 5/2006 | Tanaka et al. |
| 7,280,683 | B2 | 10/2007 | Bi et al. |
| 7,388,972 | B2 | 6/2008 | Kitson |
| 7,394,946 | B2 | 7/2008 | Dewaele |
| 7,547,307 | B2 | 6/2009 | Carson et al. |
| RE40,914 | E | 9/2009 | Taylor et al. |
| 7,837,621 | B2 | 11/2010 | Krause et al. |
| 7,967,868 | B2 | 6/2011 | White et al. |
| 8,055,487 | B2 | 11/2011 | James |
| 8,157,800 | B2 | 4/2012 | Vvedensky et al. |
| 8,257,353 | B2 | 9/2012 | Wong et al. |
| 8,265,949 | B2 | 9/2012 | Haddad |
| 8,296,094 | B2 | 10/2012 | Harrison et al. |
| 8,311,306 | B2 | 11/2012 | Pavlovskaia et al. |
| 8,333,766 | B2 | 12/2012 | Edelhauser et al. |
| 8,419,732 | B2 | 4/2013 | Mullaney |
| 8,439,914 | B2 | 5/2013 | Ross et al. |
| 8,484,001 | B2 | 7/2013 | Glozman et al. |
| 8,617,171 | B2 | 12/2013 | Park et al. |
| 8,654,150 | B2 | 2/2014 | Haskell |
| 8,715,291 | B2 | 5/2014 | Park et al. |
| 8,731,885 | B2 | 5/2014 | Iannotti et al. |
| 8,737,700 | B2 | 5/2014 | Park et al. |
| 8,777,946 | B2 | 7/2014 | Lindahl et al. |
| 8,860,753 | B2 | 10/2014 | Bhandarkar et al. |
| 8,864,750 | B2 | 10/2014 | Ross et al. |
| 8,864,763 | B2 | 10/2014 | Murray et al. |
| 8,923,590 | B2 | 12/2014 | Chen et al. |
| 8,945,128 | B2 | 2/2015 | Singh et al. |
| 8,952,986 | B2 | 2/2015 | Haskell |
| 9,101,398 | B2 | 8/2015 | Singh et al. |
| 9,204,937 | B2 | 12/2015 | Edelhauser et al. |
| 9,524,581 | B2 | 12/2016 | Haskell |
| 9,724,129 | B2 * | 8/2017 | Edelhauser ............ A61B 17/62 |
| 2002/0010465 | A1 | 1/2002 | Koo et al. |
| 2003/0191466 | A1 | 10/2003 | Austin et al. |
| 2004/0039259 | A1 | 2/2004 | Krause et al. |
| 2004/0068187 | A1 * | 4/2004 | Krause ................ A61B 17/15 |
| | | | 600/443 |
| 2004/0073211 | A1 | 4/2004 | Austin et al. |
| 2004/0073212 | A1 | 4/2004 | Kim |
| 2005/0004451 | A1 | 1/2005 | Vilsmeier et al. |
| 2005/0054917 | A1 | 3/2005 | Kitson |
| 2005/0215997 | A1 | 9/2005 | Austin et al. |
| 2005/0267360 | A1 | 12/2005 | Birkenbach et al. |
| 2006/0015120 | A1 | 1/2006 | Richard et al. |
| 2006/0079745 | A1 | 4/2006 | Viswanathan |
| 2006/0161052 | A1 | 7/2006 | Colombet et al. |
| 2006/0189842 | A1 | 8/2006 | Hoeg et al. |
| 2006/0276786 | A1 | 12/2006 | Brinker |
| 2007/0055234 | A1 | 3/2007 | McGrath et al. |
| 2007/0078678 | A1 | 4/2007 | DiSilvestro et al. |
| 2007/0133845 | A1 | 6/2007 | Fradkin et al. |
| 2007/0219561 | A1 | 9/2007 | Lavallee et al. |
| 2008/0051779 | A1 | 2/2008 | Mackenzie et al. |
| 2008/0108912 | A1 | 5/2008 | Node-Langlois |
| 2008/0119719 | A1 * | 5/2008 | Ascenzi ................ G06T 7/0012 |
| | | | 600/410 |
| 2008/0137923 | A1 | 6/2008 | Spahn |
| 2008/0177203 | A1 | 7/2008 | von Jako |
| 2008/0198966 | A1 | 8/2008 | Hjarn et al. |
| 2008/0234554 | A1 | 9/2008 | Vvedensky et al. |
| 2008/0243127 | A1 | 10/2008 | Lang et al. |
| 2008/0275467 | A1 | 11/2008 | Liao et al. |
| 2008/0319448 | A1 | 12/2008 | Lavallee et al. |
| 2009/0054887 | A1 | 2/2009 | Podhajsky |
| 2010/0036393 | A1 | 2/2010 | Unsworth |
| 2010/0087819 | A1 | 4/2010 | Mullaney |
| 2010/0130858 | A1 | 5/2010 | Arai et al. |
| 2010/0286995 | A1 | 11/2010 | Pekar et al. |
| 2011/0004199 | A1 | 1/2011 | Ross et al. |
| 2011/0009868 | A1 | 1/2011 | Sato |
| 2011/0029116 | A1 * | 2/2011 | Jordan ................ A61B 17/155 |
| | | | 700/98 |
| 2011/0103556 | A1 | 5/2011 | Carn |
| 2011/0103676 | A1 | 5/2011 | Mullaney |
| 2011/0116041 | A1 | 5/2011 | Hartung et al. |
| 2011/0188726 | A1 | 8/2011 | Nathaniel et al. |
| 2011/0304332 | A1 | 12/2011 | Mahfouz |
| 2011/0313418 | A1 | 12/2011 | Nikonovas |
| 2011/0313419 | A1 | 12/2011 | Mullaney |
| 2011/0313424 | A1 | 12/2011 | Bono et al. |
| 2012/0130687 | A1 | 5/2012 | Otto et al. |
| 2012/0155732 | A1 | 6/2012 | Finkelstein et al. |
| 2012/0214121 | A1 * | 8/2012 | Greenberg ............ A61B 5/0088 |
| | | | 433/24 |
| 2012/0328174 | A1 | 12/2012 | Jadiyappa |
| 2012/0330312 | A1 | 12/2012 | Burgherr et al. |
| 2013/0089253 | A1 * | 4/2013 | Chabanas ............ G06T 17/30 |
| | | | 382/131 |
| 2013/0096373 | A1 | 4/2013 | Chabanas et al. |
| 2013/0121612 | A1 | 5/2013 | Falco, Jr. et al. |
| 2013/0172783 | A1 | 7/2013 | Ikits et al. |
| 2013/0201212 | A1 | 8/2013 | Haskell |
| 2013/0211792 | A1 * | 8/2013 | Kang .................... G16H 50/50 |
| | | | 703/1 |
| 2014/0039663 | A1 | 2/2014 | Boyer et al. |
| 2014/0073907 | A1 | 3/2014 | Kumar et al. |
| 2014/0189508 | A1 | 7/2014 | Granchi et al. |
| 2014/0236153 | A1 * | 8/2014 | Edelhauser ............ A61B 17/62 |
| | | | 606/56 |
| 2014/0270437 | A1 | 9/2014 | Shreiber et al. |
| 2014/0303486 | A1 | 10/2014 | Baumgartner et al. |
| 2014/0324403 | A1 | 10/2014 | Gotte |
| 2014/0328460 | A1 | 11/2014 | Egli et al. |
| 2014/0343586 | A1 | 11/2014 | Sakuragi |
| 2014/0350389 | A1 | 11/2014 | Powell et al. |
| 2014/0357984 | A1 | 12/2014 | Wallace et al. |
| 2014/0379356 | A1 | 12/2014 | Sachdeva et al. |
| 2015/0049083 | A1 | 2/2015 | Bidne et al. |
| 2015/0087965 | A1 | 3/2015 | Tokuda et al. |
| 2015/0238271 | A1 * | 8/2015 | Wollowick ............ A61B 6/12 |
| | | | 600/436 |
| 2016/0045225 | A1 | 2/2016 | Edelhauser et al. |
| 2016/0331463 | A1 | 11/2016 | Notzli et al. |
| 2017/0281233 | A1 | 10/2017 | Edelhauser et al. |

FOREIGN PATENT DOCUMENTS

| | | |
|---|---|---|
| RU | 2448663 C1 | 4/2012 |
| RU | 2471447 C1 | 1/2013 |
| RU | 2489106 C2 | 8/2013 |
| WO | 2009076296 A2 | 6/2009 |
| WO | WO 2009/076296 A2 * | 6/2009 ........... A61B 17/155 |

(56) References Cited

FOREIGN PATENT DOCUMENTS

| WO | 2010104567 A1 | 9/2010 |
|----|---------------|--------|
| WO | 2013013170 A1 | 1/2013 |

OTHER PUBLICATIONS

Craveiro-Lopes, MD, Software Assisted "Ortho-SUV Frame", Int'l Congress on External Fixation & Bone Reconstruction, Oct. 22, 2010.

European Patent Office (ISA), International Search Report and Written Opinion dated Jun. 25, 2013 for International Application No. PCT/US2013/024548, International filing date Feb. 3, 2013.

IMED Surgical, Adam Frame with Paley's Method, Workshop, Oct. 2010.

LITOS GmbH, "Ilizarov Hexapod System," available from http://d3llyibkg2zj6z.cloudfront.net/ImagemAnexo/Ilozarov-Hexapod-System.—PDF, dated May 23, 2007.

Response Ortho LLC, Smart Correction Computer Assisted Circular Hexapod System Brochure, date not known.

Smart Correction, Computer-Assisted Circular External Fixator System, website printout, Feb. 2, 2011.

Vreden Russian Research Institute of Traumatology and Orthopedics Ortho-SUV Ltd., Deformity Correction and Fracture Treatment by Software-based Ortho-SUV Frame, Saint-Petersburg, 2013.

Extended European Search Report for Application No. EP17173905, dated Oct. 30, 2017.

\* cited by examiner

SOFTWARE FOR USE WITH DEFORMITY CORRECTION

FIELD OF THE INVENTION

The present disclosure relates to software used in planning the correction of bone deformities preoperatively and/or postoperatively, and in particular relates to autonomously or semi-autonomously creating virtual models to create the correction plan.

BACKGROUND OF THE INVENTION

Currently, external fixation systems may be used to correct skeletal deformities using the distraction osteogenesis process, for example. The Ilizarov external fixation device (or similar system) may be used for such a purpose. The Ilizarov-type devices generally translate bone segments by manipulating the position of rings connected to each bone segment.

These external fixation devices generally utilize threaded rods fixated to through-holes in the rings to build the frame. In order to build the desired frame, these rods generally have to have different lengths. Once the frame is installed, the patient or surgeon moves the rings or percutaneous fixation components manually or mechanically by adjusting a series of nuts.

As fixation devices become more complex, the task of determining the optimal lengths and positions of the struts with respect to rings of the fixation frame, as well as creating a correction plan for manipulating the struts to correct the bone deformity, becomes more difficult.

The increasing difficulty of these determinations decreases the attractiveness of using complex fixation frames. It would be advantageous to have an at least partially automated method for determining the optimal configuration of a fixation frame in reference to a deformed bone, as well as a correction plan for manipulating the fixation frame to correct the bone deformity.

BRIEF SUMMARY OF THE INVENTION

According to a first embodiment of the disclosure, a method of generating a correction plan for correcting a deformed bone includes inputting to a computer system a first image of the deformed bone in a first plane and inputting to the computer system a second image of the deformed bone in a second plane. Image processing techniques are employed to identify a plurality of anatomical landmarks of the deformed bone in the first image. The first image of the deformed bone is displayed on a display device. A graphical of the deformed bone is autonomously generated and graphically overlaid on the first image of the deformed bone on the display device, the graphical template including a plurality of lines, each line connected at each end to a landmark point corresponding to one of the anatomical landmarks. A model of the deformed bone may be autonomously generated based on the graphical template. A first model fixation ring having a first position and orientation and a second model fixation ring having a second position and orientation may be generated and displayed on the display device. At least one of the position and orientation of at least one of the model fixation rings may be graphically manipulated.

Combinations of sizes of a plurality of model struts to connect the models of the first and second fixation rings may be determined with an algorithm using the position and orientation of the first and second model fixation rings. A first position for a limiting anatomical structure may be input to the computer system, the limiting anatomical structure defining a location having a maximum distraction value. During the step of inputting the first position for the limiting anatomical structure, the model rings and the model struts may be simultaneously displayed on the display device and overlap the first image of the deformed bone on the display device. During the step of inputting the first position for the limiting anatomical structure, the first image of the deformed bone may include visible soft tissue structures. The limiting anatomical structure may be input graphically using an input device, which may be a computer mouse. A second position for the limiting anatomical structure may be input to the computer system while the model rings and the model struts are simultaneously displayed on the display device and overlap the second image of the deformed bone on the display device, the second image of the deformed bone including visible soft tissue structures.

Each landmark point of the graphical template may be configured to be repositioned via an input device. Upon repositioning one of the landmark points, each line connected to the repositioned landmark point may remain connected to the repositioned landmark point.

The first image of the deformed bone may be an x-ray image displayed on the visual medium in one of an anterior-posterior and a lateral view, and the second image of the deformed bone may be an x-ray image displayed on the visual medium in the other of an anterior-posterior and a lateral view. The first and second images of the deformed bone may include images of physical rings and physical struts of an external fixation frame coupled to a patient. A position and orientation of the physical rings and a length and orientation of the physical struts may be autonomously determined based on the first and second images. The determined position and orientation of the physical rings and the determined length and orientation of the physical struts may be displayed on the visual medium. At least one of the determined position and the determined orientation of at least one of the physical rings may be graphically manipulated. The determined orientation of at least one of the struts may be graphically manipulated.

DETAILED DESCRIPTION

In one embodiment of the disclosure, software aids a user, such as a physician, surgeon, or other medical personnel, in planning and carrying out the correction of a bone deformity using a limb reconstruction frame using a web application, for example. Other software for creating a correction plan for an external fixation frame is described in U.S. Patent Publication No. 2014/0236153, the contents of which are hereby incorporated by reference herein.

Upon starting the application, the user is presented with a login screen. The login screen preferably includes a username field and password field in which the user enters, respectively, a username and password to gain further access to the application. This step of authentication may, for example, help maintain compliance with patient privacy regulations. In cases where a first time user tries to gain further access to the application, a new user account may have to be created.

Figure 1:
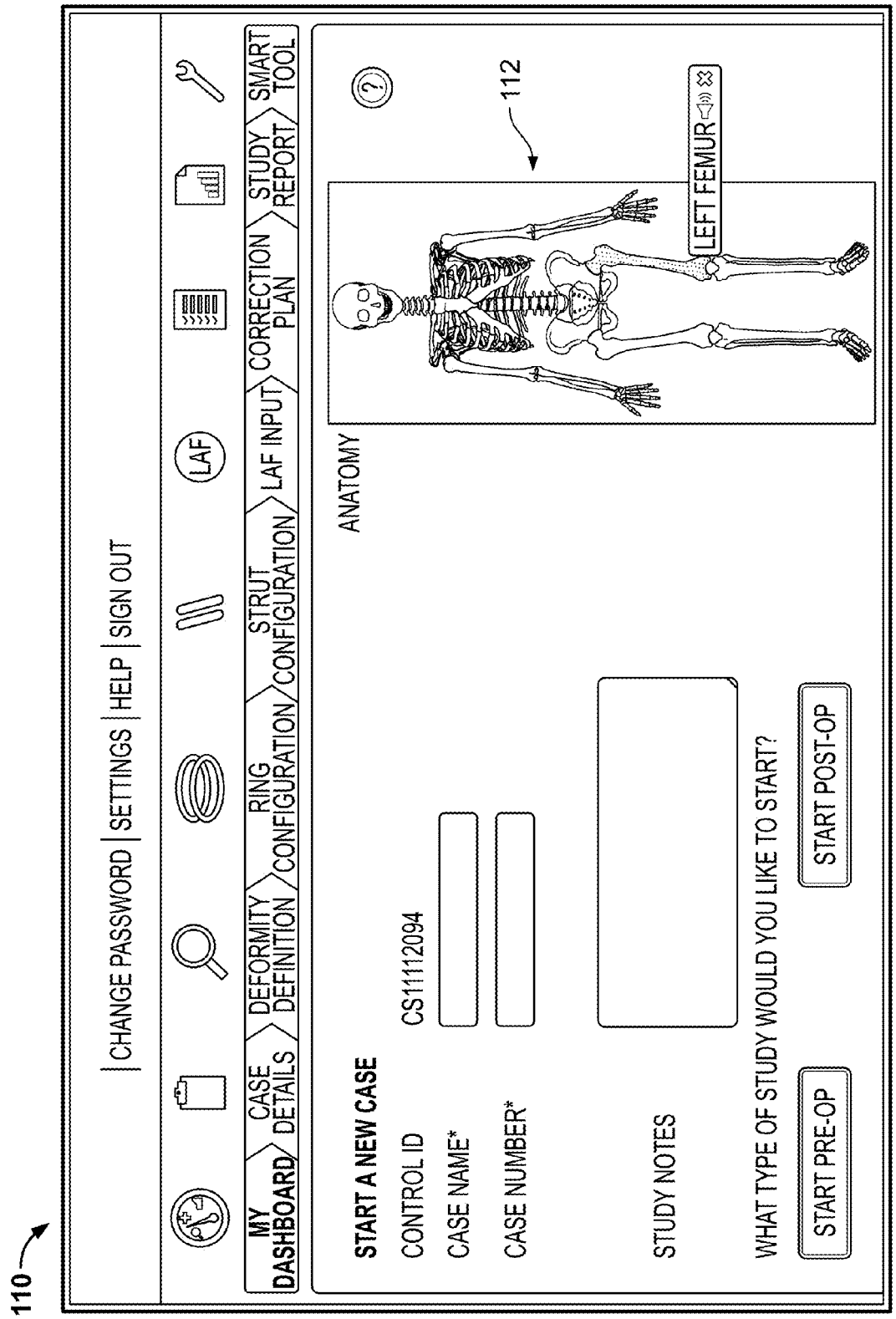
FIG. 1 illustrates a home page screen of a deformity correction application.

As shown in FIG. 1, upon logging in, the user is taken to the home screen 110. From the home screen 110, the user has the option of starting a new case for a patient whose information has not yet been entered into the software. Prior to starting the new case, the user may enter a case name and/or number for later reference, and may also enter any desired notes regarding the case to be saved with the case. A skeletal representation 112 may also be provided, for example on the home screen 110, so that the user may select the relevant bone. As shown in FIG. 1, the left femur has been selected. With the desired anatomy entered, and the relevant case name and number information entered, the user may choose to begin the case as a pre-op case or a post-op case, with each procedure being described separately below. Generally speaking, the pre-op mode is used prior to the surgical fixation of the limb reconstruction device to the deformed bone. The post-op mode is to be used after the limb reconstruction device, with associated rings and struts, has already been affixed to the patient. In a single case, the pre-op mode can be used alone, the post-op mode can be used alone, or each mode can be used prior to and following surgery, respectively.

After the user begins the case as a pre-op case, the user may be brought to a case details screen which may allow entering, viewing, or modifying patient details such as the patient's name, gender, race, date of birth, anatomy relevant to the case, and notes as the user sees fit. With the case details entered as desired, the user may begin a deformity definition procedure.

Figure 2A:
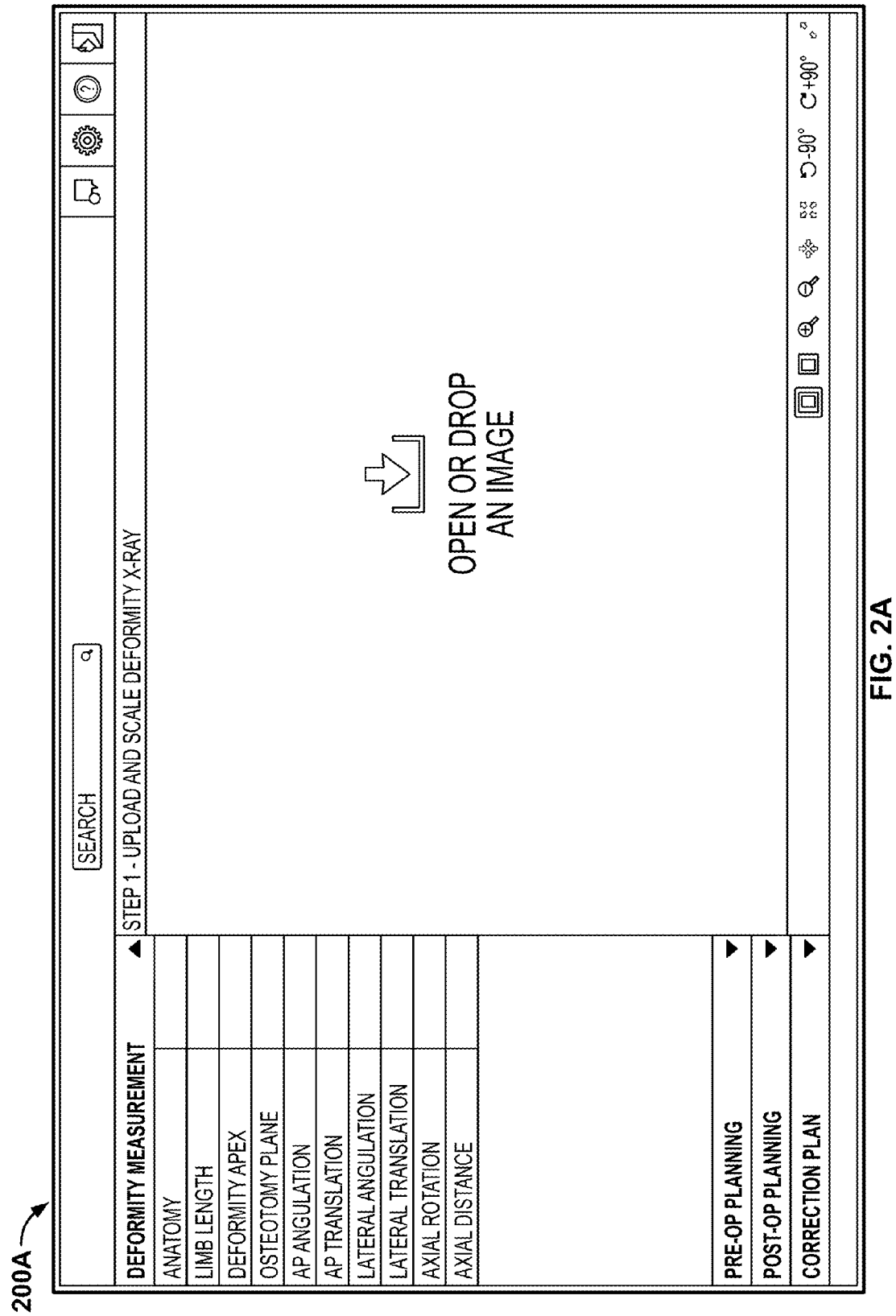
FIGS. 2A-I illustrate various deformity definition screens of the deformity correction application.
Figure 2B:
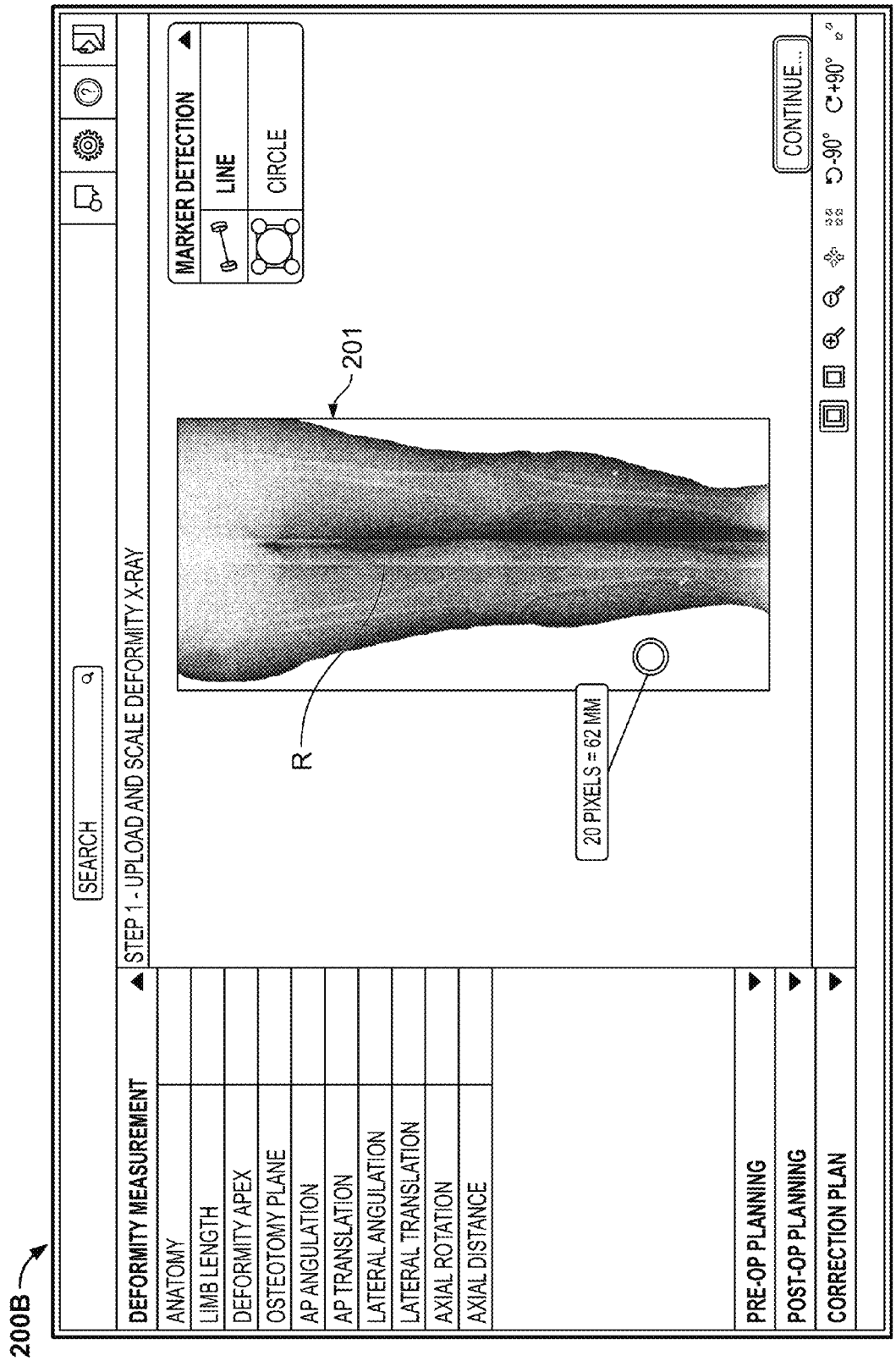

The user may be initially presented with a first deformity definition screen 200A, as shown in FIG. 2A, which may prompt a user to open or otherwise load one or more medical images, such as X-ray images, onto the application. Although described herein in terms of X-ray images, it should be understood that other types of medical images, such as "slices" of a CT-scan, may also be used with the methods and systems described herein. It should also be understood that multiple medical images, such as images of the same anatomy in different views (e.g. anterior-posterior view and lateral view) may be loaded to the application. This may be accomplished by any number of suitable methods, for example by choosing one or more image files that have been previously saved to memory on the computer running the application. In the pre-op mode, there will generally not be a fixation device shown, as the fixation device hast not yet been implanted onto the patient. Once chosen, the medical image 201, for example as shown in FIG. 2B, may be shown on a second deformity definition screen 200B. These medical images 201 may help the user to define the bone deformity, described more fully below. Before, during, or after uploading, the user also may provide details relating to the image 201, such as the view (e.g. lateral plane) in which the image was taken. With the image 201 shown on screen 200B, the user may scale the image 201 to the application. For example, a size reference R, such as a ruler, may be included in the image 201, so that the user may scale a measurement unit in the application (e.g. a pixel) to a real measurement unit represented in the image 201 (e.g. a millimeter). This step may be performed by the user by selecting a drawing tool, such as a line or circle, and creating a drawing on the image, preferably in relation to the size reference R. The user may enter the measurement of the drawn line (or other geometry) that represents the real measurement value, which the application may then correlate to the application measurement unit. Alternately, this scaling step may be performed automatically, for example by the application recognizing a defining characteristic of the size reference R, which may be compared to a real measurement value already stored in the application.

Figure 2C:
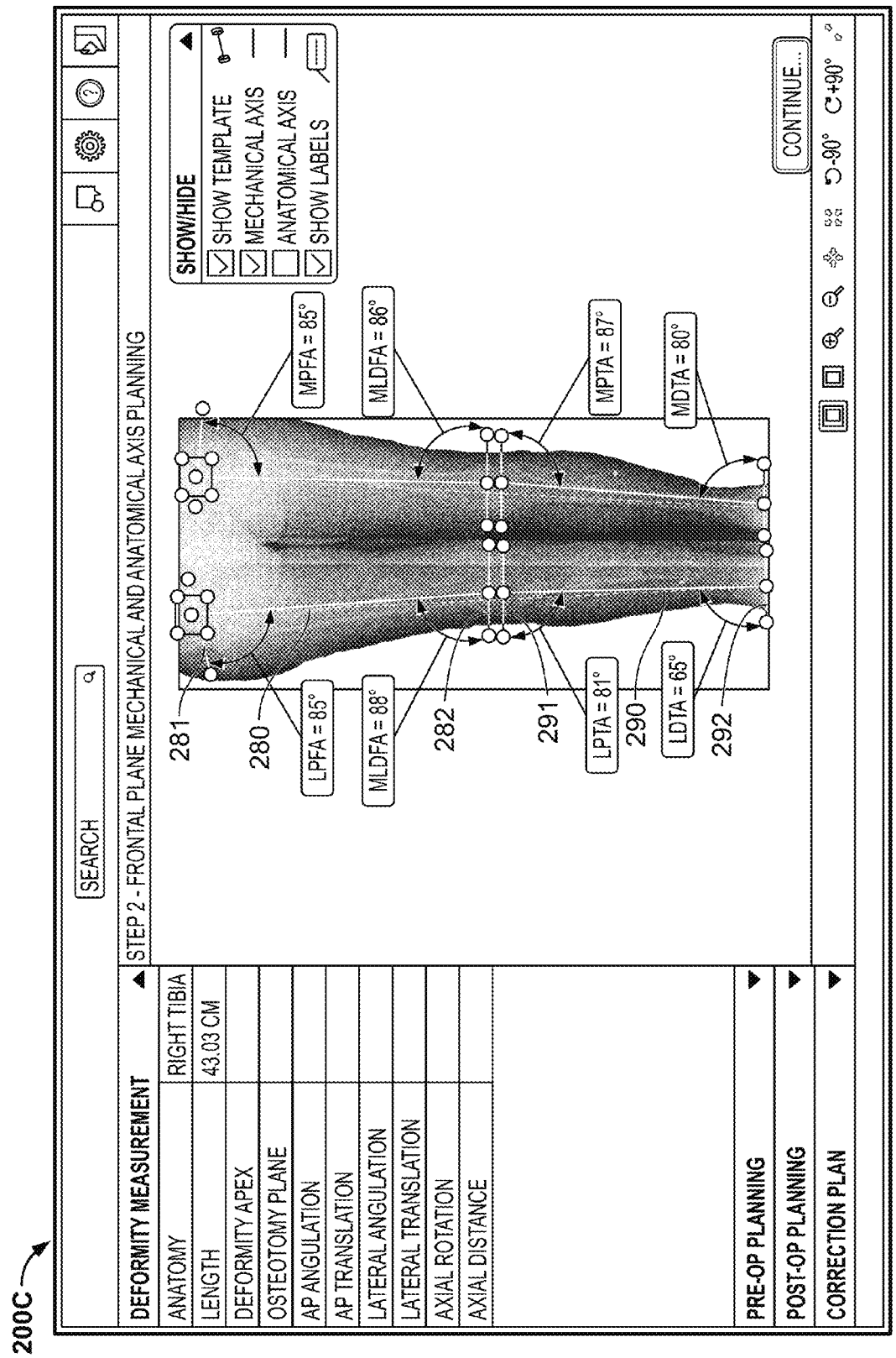
Figure 2D:
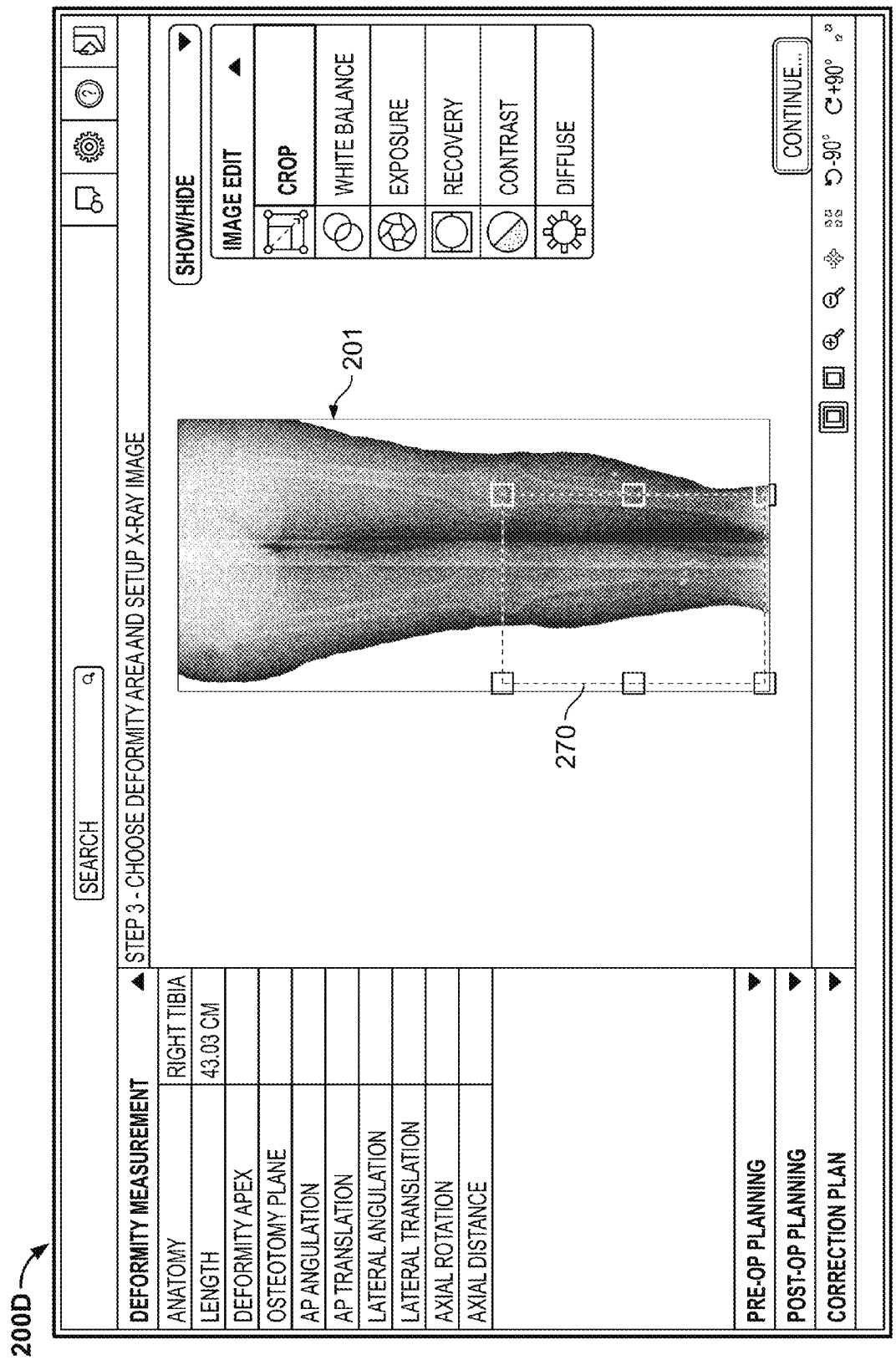
Figure 2E:
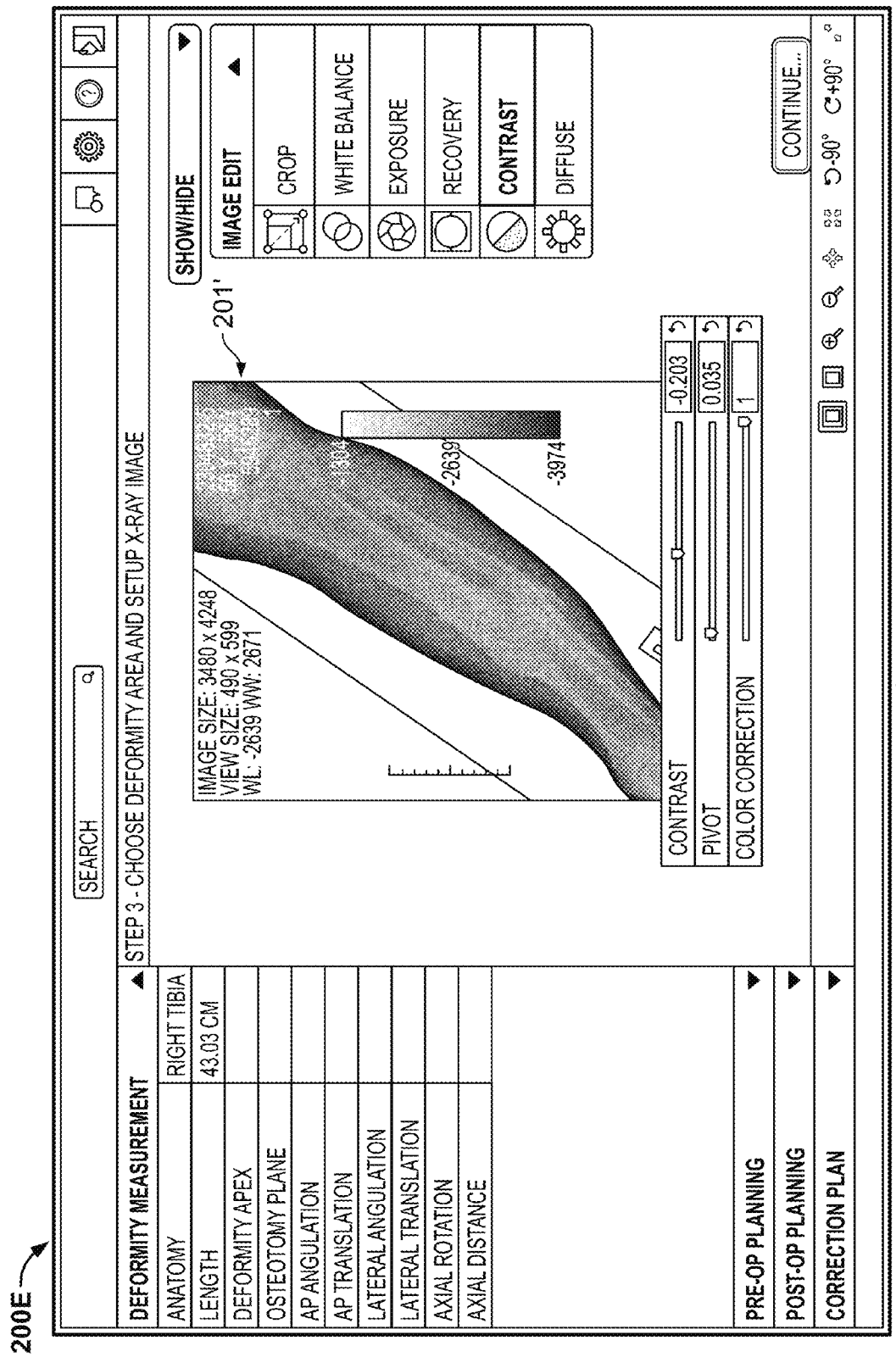

With the image 201 uploaded and scaled, relevant axes of the anatomy may be defined, either autonomously or semi-autonomously. For example, as shown in FIG. 2C, a user may define, aided by the application, the mechanical and/or anatomical axes of the bone(s) against the backdrop of image 201 on screen 200C. For example, as shown in FIG. 2C, the user may select the "mechanical axis" radio button on screen 200C and using an input device, may define relevant anatomic landmarks. For example, upon selecting the "mechanical axis" radio button, one (or two) femoral mechanical axis indicia and one (or two) tibial mechanical axis indicia may appear on the image 201.

In the illustrated embodiment, two mechanical femoral axis indicia take the form of lines 280, and two mechanical tibial axis indicia take the form of lines 290. Each line 280, 290 may include an endpoint that the user can drag to a different position on the image 201 to help define the relevant axes. For example, to define the mechanical femoral axis, the user may drag a first end of line 280 to a center of the femoral head on one leg and the other end of line 280 to the articular surface of the distal femur, and the process may be repeated for the other leg if desired. Similarly, to define the mechanical tibial axis, the user may drag a first end of line 290 to the articular surface of the proximal tibia and the other end of line 290 to the center of the ankle joint. Based on the placement of lines 280 and 290, the application may calculate and display relevant mechanical axes measurement, for example including, the lateral proximal femoral angle ("LPFA"), the mechanical lateral distal femoral angle ("mLDFA"), the lateral proximal tibial angle ("LPTA"), and the lateral distal tibial angle ("LDTA"), although other relevant measurements may also be calculated and displayed. In order to make these measurements, additional lines must be provided. For example, the LPFA is measured as the angle between the line joining the trochanteric tip to the femoral head center 281 and the femoral mechanical axis as represented by line 280. Similarly the mLDFA is measured as the angle that a condylar tangent line 282 makes with the line representing the femoral mechanical axis as represented by line 280. Lines 281 and 282 may be displayed on the medical image 201 and manipulated as desired. With regard to the tibial angles, the LPTA is measured laterally as the angle between a tibial plateau tangent line 291 and the line representing the tibial mechanical axis 290, while the LDTA is measured laterally as the intercept of a tibial articular plafond line 292 with the line representing the tibial mechanical axis 290. Lines 291 and 292 may also be displayed on the medical image 201 and manipulated by the user. Although the steps above are described as manual placement of lines 280-282 and 290-292, it should be understood that the application may automatically recognize the relevant landmarks and place the lines on the image 201, with the user having the ability to modify the placement of lines 280-282 and 290-292 if such placement is incorrect. As should be understood, the process may be repeated for each leg if two legs are shown in medical image 201. The application may also compare the calculated angles described above to a range of values considered normal, which may be stored in memory, and highlight or otherwise indicate to the user any calculated angle falling outside the range. As shown in FIG. 2, the LDTA of the leg with the deformed tibia is calculated as 65°, which is outside a range considered normal, which may be for example between 86° and 92°, leading to the abnormal LDTA being highlighted.

On a fourth deformity definition screen 200D, the user may select the area of interest on the medical image 201 for measuring deformity parameters in a following step. For example, a rectangle 270 (or other shape) may be overlaid on the medical image 201 with the option for the user to resize and/or reposition the rectangle 270 to select the relevant deformed anatomy that is to be corrected. With the relevant area selected, the image 201 may be modified, for example by cropping the image so that only the relevant deformed anatomy is displayed, as shown on screen 200E of FIG. 2E. The cropped image 201' may be further modified with a number of image processing features, including, for example, resizing, repositioning (e.g. rotating), or changing the contrast of the cropped image 201'. In one example, the user may apply an exposure filter to minimize or eliminate the tissue region shown in the cropped image 201' for a better view of the deformed bone. Once the cropped image 201' is edited as desired, the user may further define the deformity.

Figure 2F:
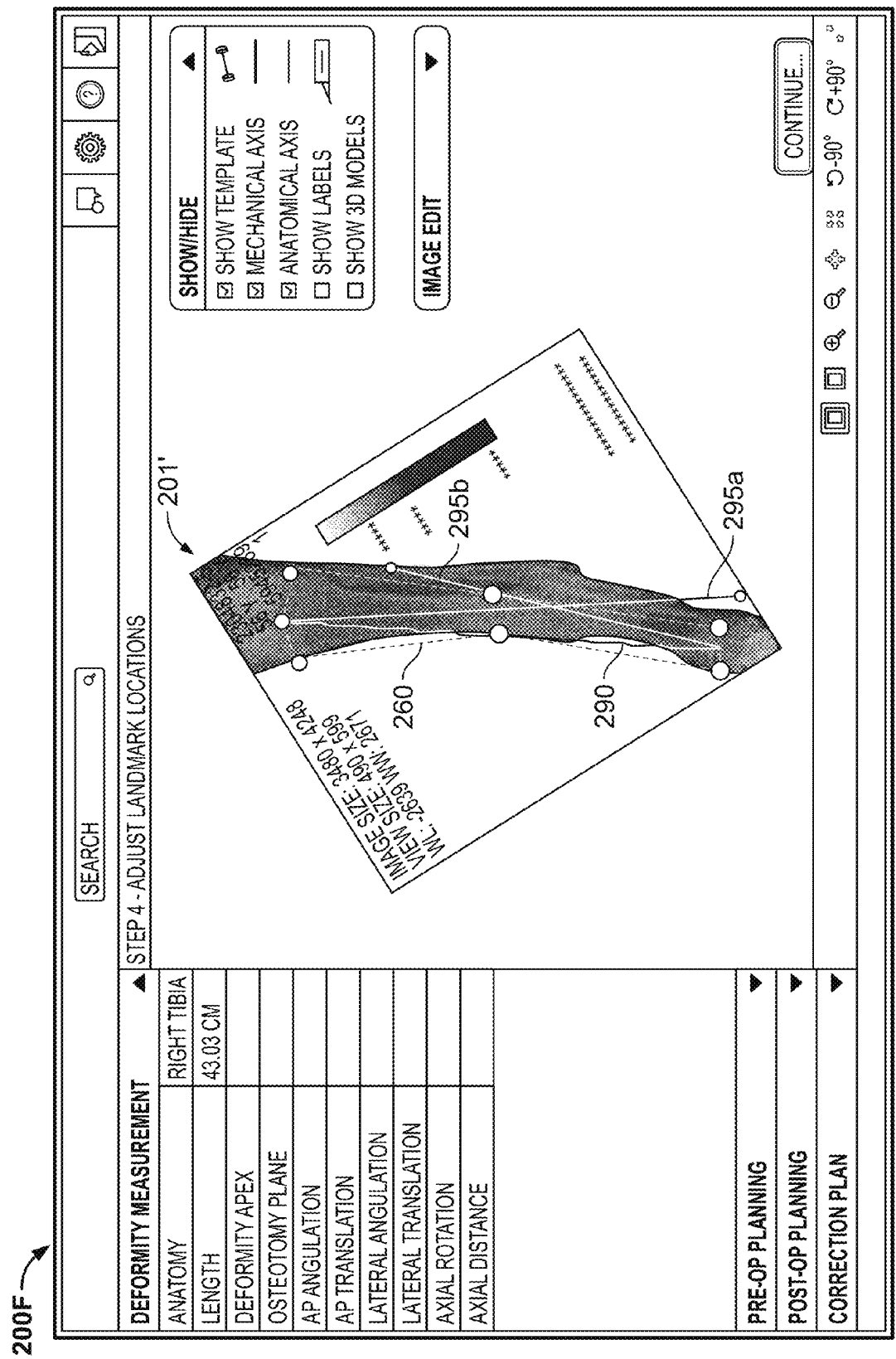

The cropped image 201' of the deformed right tibia is illustrated in FIG. 2F on a new screen 200F after being rotated and filtered. On screen 200F, the mechanical tibia axis 290 from screen 200C may be displayed, along with an anatomical axis 295a of the proximal tibia and an anatomical axis 295b of the distal tibia, the axes 295a and 295b being different due to the deformity. As with the mechanical tibial axis 290 described above, the lines representing the anatomical axes 295a, 295b, may be automatically placed on the cropped image 201', for example based upon landmarks of the tibia, with the user having the option to modify the position of the lines 295a, 295b. In addition to the tibial mechanical axis 290 and the anatomical axes 295a, 295b, a template 260 may be displayed on the cropped image 201' to identify landmarks on the deformed tibia. The template 260 includes a plurality of landmark points corresponding to anatomical landmarks. In the illustrated example, the template 260 including the medial and lateral edges of the proximal tibial, the center of the proximal tibia, the medial and lateral edges of the distal tibia, and medial and lateral surfaces of the location of the deformity in the tibia. The template 260 may be automatically placed on the cropped image 201', for example based upon landmarks of the tibia, with the user having the option of moving one or more of the landmark points to a different position on the cropped image 201', resulting in the connecting lines repositioning and altering the shape of template 260. In other words, upon repositioning one of the landmark points, each line connected to the repositioned landmark point remains connected to the repositioned landmark point.

Figure 2G:
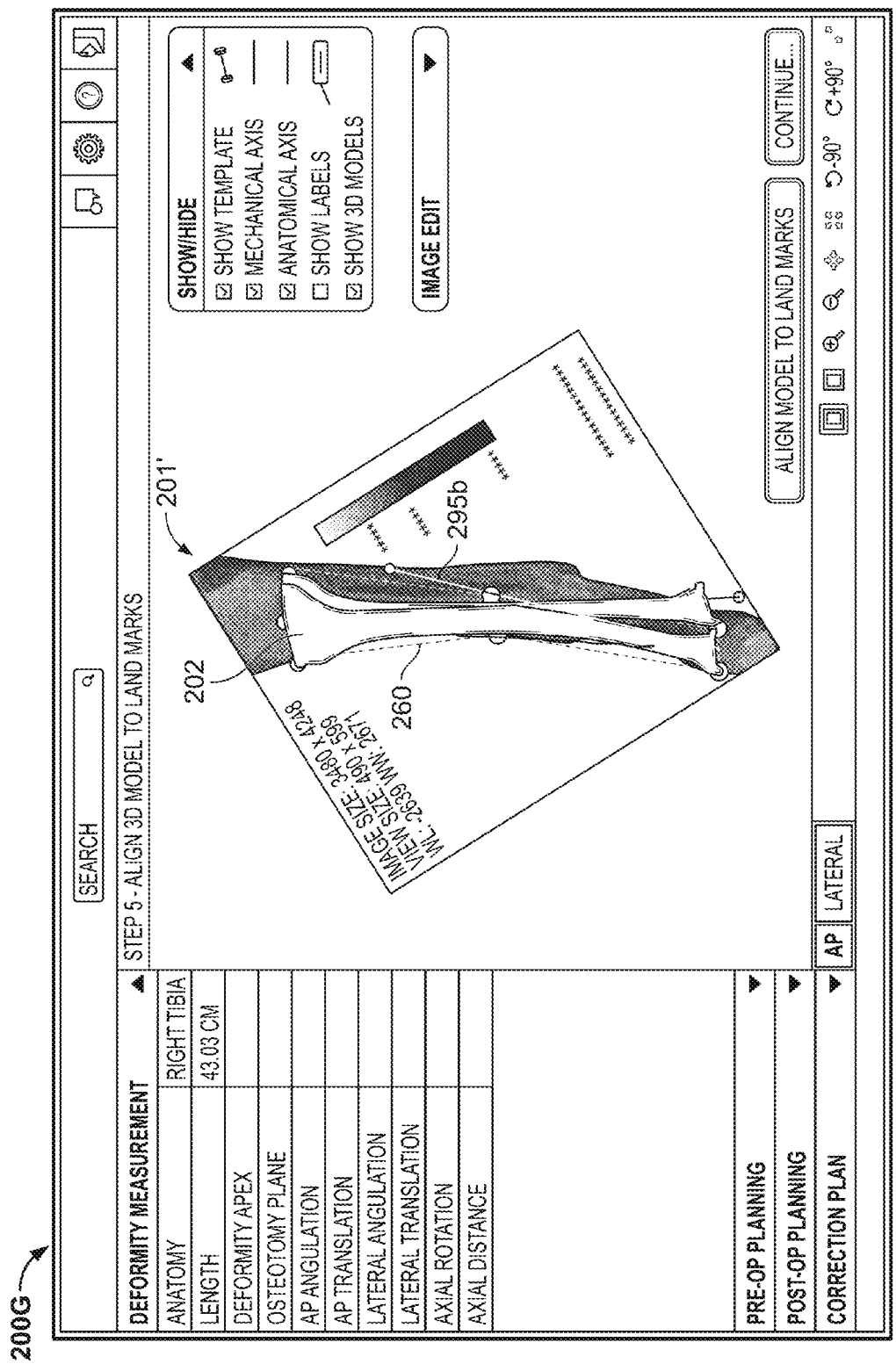
Figure 2H:
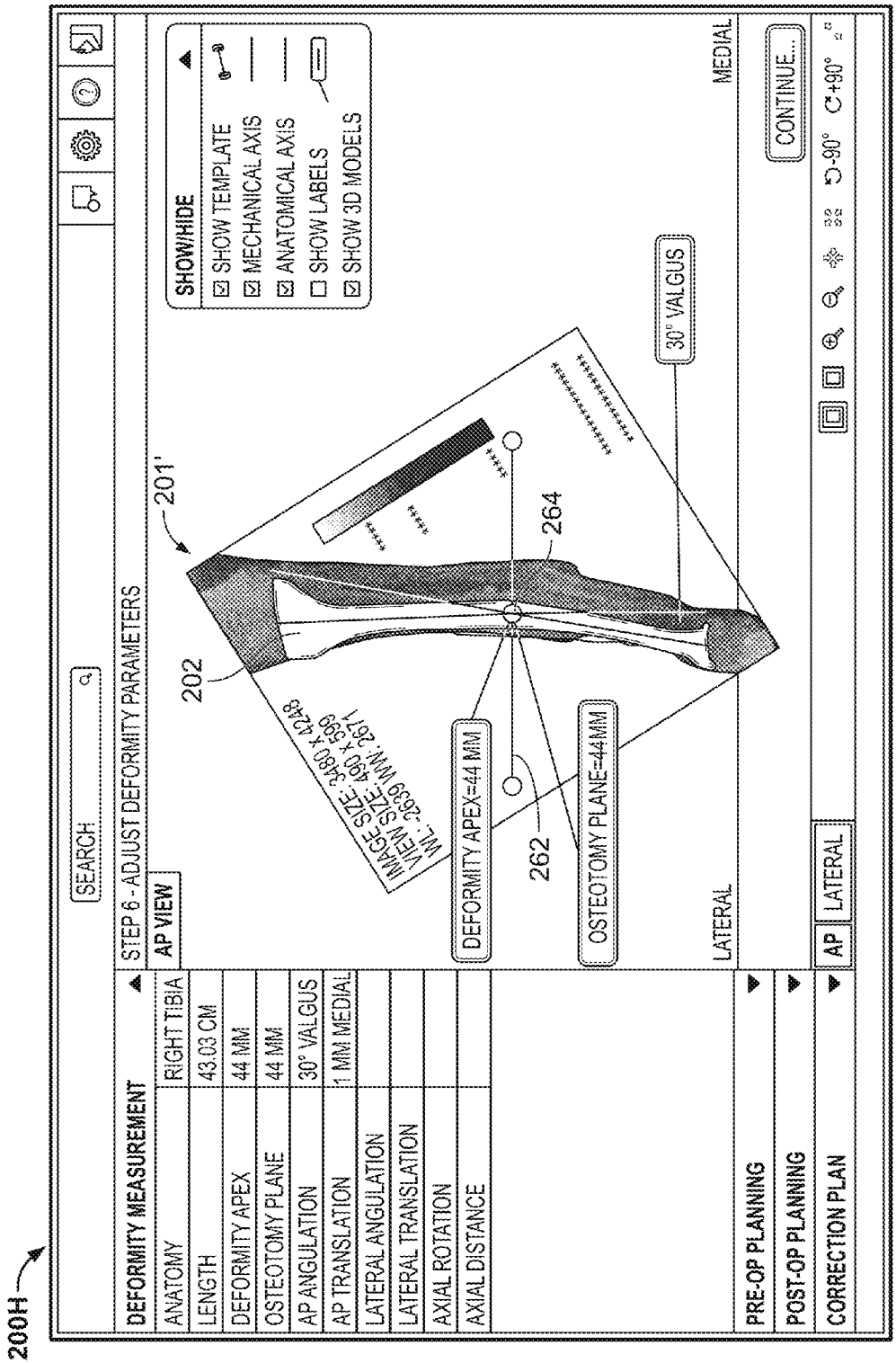

As shown in FIG. 2G, a radio button may be selected to display a model bone, in this case a model tibia 202, overlaid on the cropped image 201'. The model bone may be selected from a library of model bones based, at least in part, on the particular anatomy and patient information entered upon creating the case. A button may be clicked on screen 200G to deform the model bone 202 such that the landmarks of the model tibia align with the landmarks defined by template 260. The deformity may be further defined on deformity definition screen 200H, as shown in FIG. 2H. A line 262 representing the osteotomy plane, and a point 264 representing the deformity apex, may each be shown on the cropped image 201', whether or not the model 202 is simultaneously shown on screen 200H. The model bone 202 may include separate proximal and distal (or reference and moving) portions that may be manipulated directly by the user. For example, the user may click one of the portions of model bone 202 and drag the portion into a different position, with calculated values (e.g. angulation, translation) updating as the model bone 202 is manipulated.

Figure 2I:
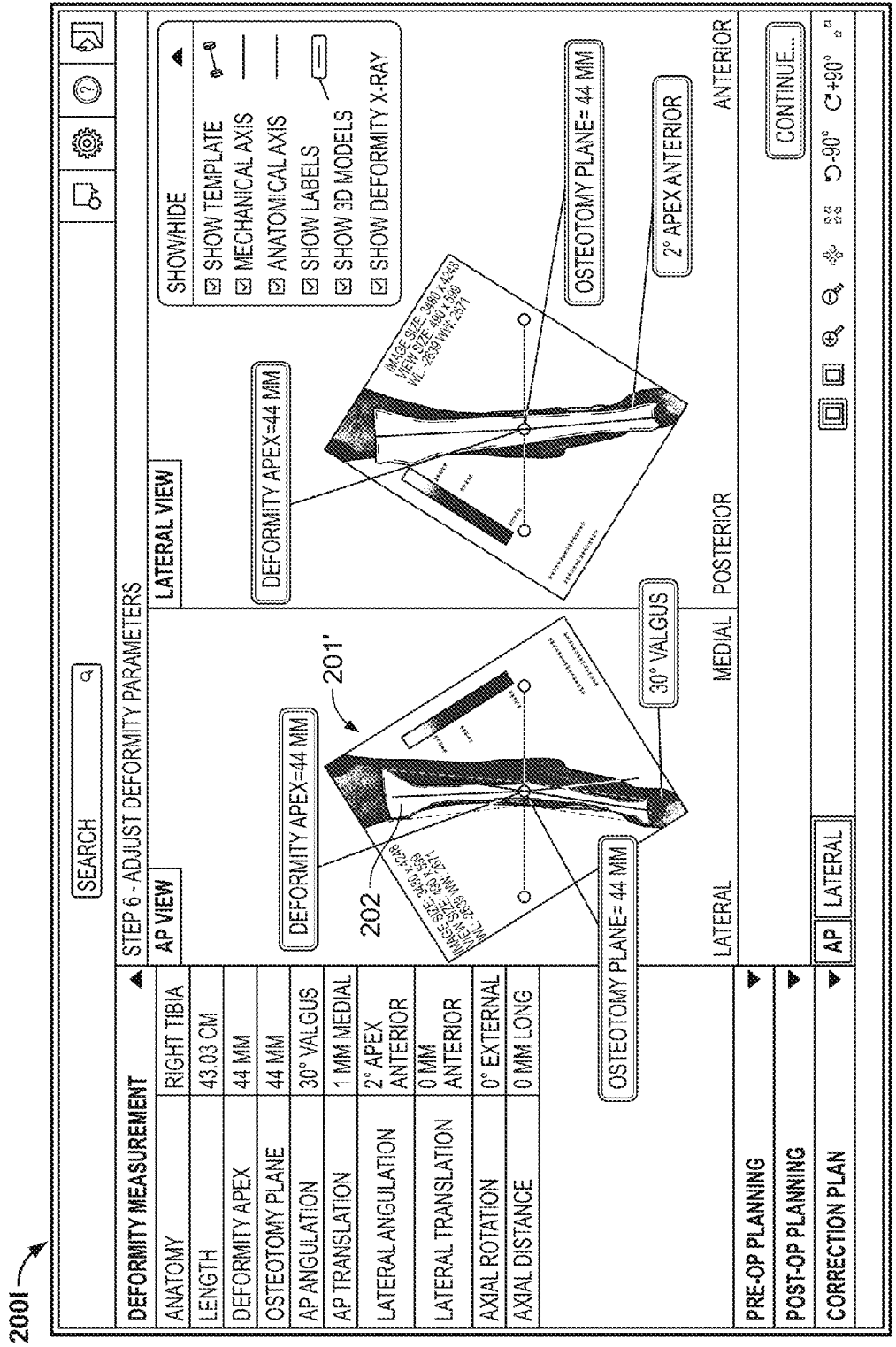

Although the deformity definition is described above with reference to a medical image 201 in an anterior-posterior plane, it is preferable that some or all of the deformity definition steps are additionally performed on a medical image in a different plane, such as a medial-lateral plane or a superior-inferior plane, for example. The medical image 201 may alternatively be viewed in axial, coronal or sagittal planes, for example. As shown in FIG. 2I, the deformed model bone 202 is shown over a cropped image 201' of the deformed tibia in an AP view and the model bone 202 is also shown on an adjacent image of the deformed tibia in a lateral view. The parameters of the model bone 202, the mechanical and anatomic axes, and the template 260 may be revised in either view to update the deformity parameters until the user is satisfied that the model bone 202 accurately reflects the patient's deformed bone. As should be understood from the above description, the system and methods described herein provide a user the ability to accurately define the deformity of the deformed bone by manipulating on-screen representations of the bone or relevant parameters or landmarks with an input device, such as a mouse, without needing to manually enter numerical values relating to the deformity.

Figure 3A:
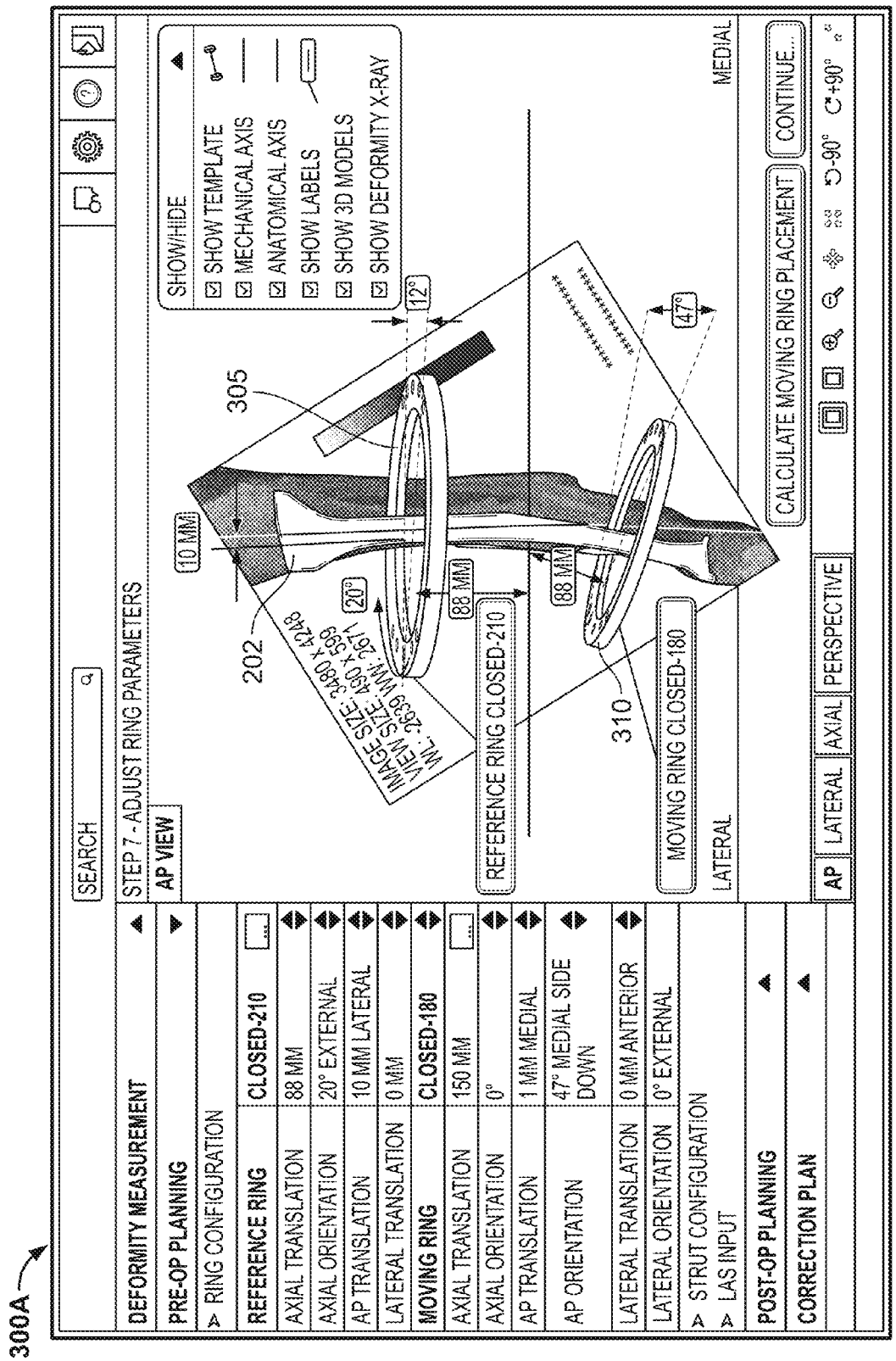
FIGS. 3A-B illustrate various ring configuration screens of the deformity correction application in a preoperative ("pre-op") mode.

Once the user is satisfied that the model bone 202 is an accurate representation of the deformed bone, the user can proceed to the first ring configuration screen 300A (FIG. 3A). At this point, the user may input the size of the desired rings, including a reference ring 305 and a moving ring 310. For example, a user may be able to choose between a 155 mm, 180 mm, or 210 mm ring. The user may also be able to choose the type of ring, such as a full ring, partial ring, open ring, or closed ring. Different types of rings are known in the art and the inclusion of different rings as options in the software is largely a matter of design choice. The rings 305, 310 are displayed along with the model bone 202 on the screen, preferably in an AP view, a lateral view, and/or an axial view. Additional views, such as a perspective view, may be included. On screen 300A, the model bone 202 and rings 305, 310 are displayed in an AP view with options to change to lateral, axial, and perspective views by choosing the corresponding tab on screen. The cropped medical image 201' is also displayed, although either the model bone 202 or the cropped image 201' may be removed by clicking the appropriate radio button on screen.

Figure 3B:
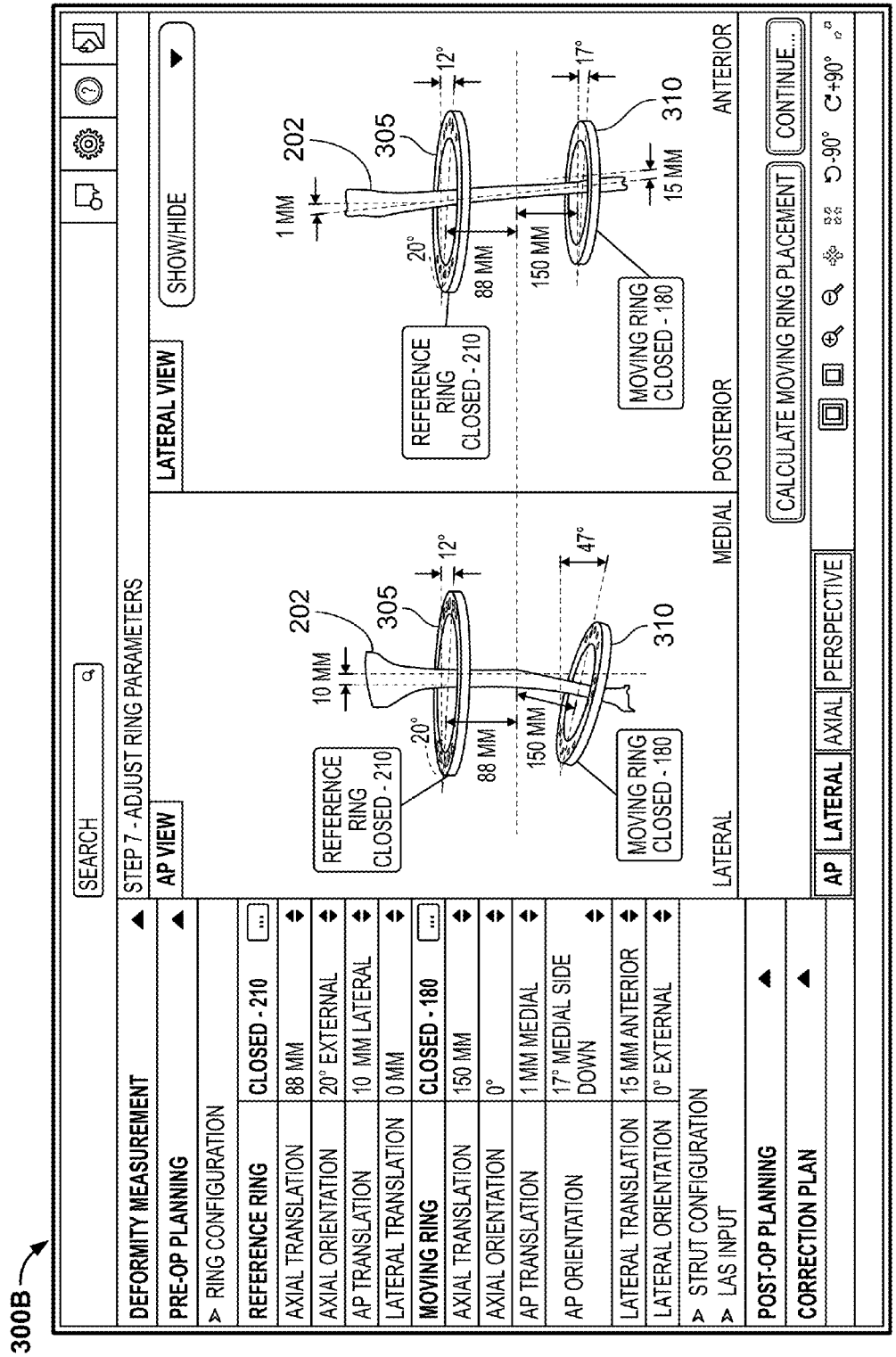

The position and orientation of portion of the model bone 202 proximal to the deformity and the portion of the model bone 202 distal to the deformity are based on the input received during the deformity definition described above. Once a size and/or type of ring is selected for the reference ring 305, it is displayed perpendicular to the reference bone fragment (in the illustrated example, the portion of the model bone 202 proximal to the deformity) with a longitudinal axis of the reference bone fragment extending through the center of the reference ring 305. Similarly, once a size and/or type of ring is selected for the moving ring 310, it is displayed perpendicular to the non-reference bone fragment (in the illustrated example, the portion of the model bone 202 distal to the deformity) with a longitudinal axis of the non-reference bone fragment extending through the center of the moving ring 310. The rings 305, 310 may also be placed with a default axial translation that can be changed. For example, the reference ring 305 may have a default axial translation of approximately 50 mm with respect to the deformity apex, while the moving ring 210 may have a default axial translation of approximately 150 mm with respect to the deformity apex. The user may enter numerical values for position and orientation parameters for the rings 305, 310, by inputting values, clicking the "up" or "down" arrows associated with the particular position or orientation, or by interacting with the rings 305, 310 on screen, for example by clicking one of the rings 305, 310 with a mouse and dragging or rotating the ring to a new position and/or orientation. Because this is the pre-op mode and no fixation devices has yet been attached to the patient, the user chooses the ring sizes, positions and orientations that he believes will be effective for the correction based, for example, on his experience and knowledge. As the values for the position and/or orientation of the rings 305, 310 are changed, the graphical representations of the rings 305, 310 changes to reflect the new values. If the rings 305, 310 are being manipulated graphically (e.g. via dragging on screen with a mouse), the numerical values associated with the position and/or orientation may update accordingly. For the reference ring 305, the position values may include an AP translation, a lateral translation, an axial translation, and an axial orientation. The moving ring 310 may include these values, and additional values may include an AP orientation and a lateral orientation. Any of the above-described values may be displayed on screen to assist the user in understanding the position of the rings 305, 310 relative to the model 202. It may be particularly useful to display only non-zero values so that the most pertinent information is displayed. The user may position multiple views of the model bone 202 and the rings 305, 310 on the screen simultaneously. For example, as shown in FIG. 3B, screen 300B illustrates the model bone 202 with rings 305, 310 positioned thereon simultaneous in the AP and lateral views with the cropped image 201' hidden.

Figure 4A:
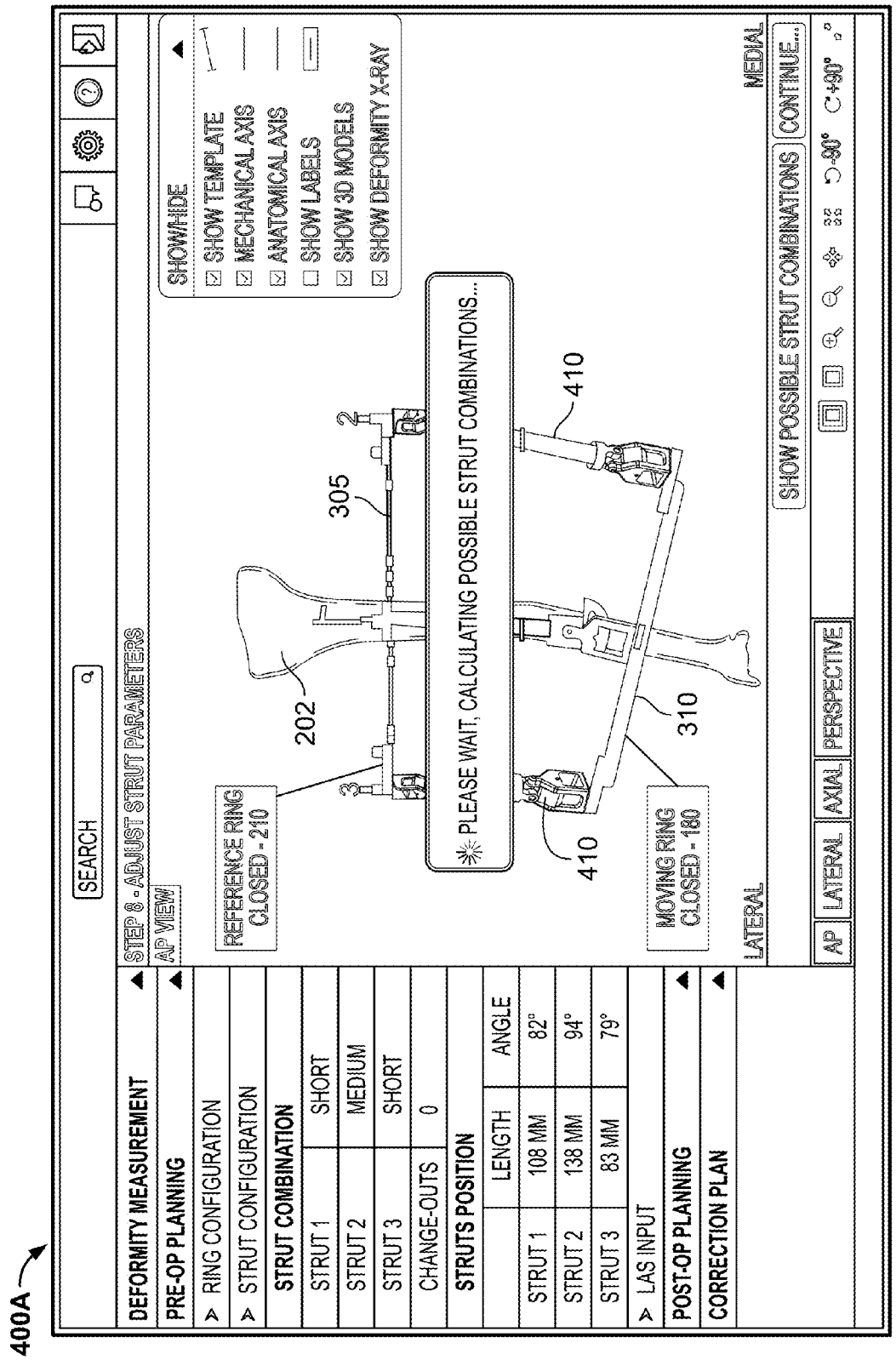
FIGS. 4A-B illustrate various strut configuration screens of the deformity correction application in the pre-op mode.

Once the user is satisfied that the reference ring 305 and moving ring 310 are at locations on the model bone 202 representative of where the actual rings should be located on the patient's deformed bone, the user can proceed to the first strut configuration screen 400A as shown in FIG. 4A. The first strut configuration screen 400A allows the user to initiate an automatic calculation of possible strut combinations to connect the reference ring 305 to the moving ring 310. Once the calculation is complete, a plurality of graphical representations of struts 410 are illustrated on the screen in their intended initial positions with respect to the graphical representation of the reference ring 305 and the moving ring 310. The user also has the option to display all of the calculated combinations of struts 410 that may be used with the external fixator. For example, although one particular combination of struts 410 is illustrated on screen, multiple combinations may be calculated as possibilities. The application may default to showing the combination of struts 410 that requires the fewest number of strut change-outs during the deformity correction, but other options may be available for the user to choose based on his or her particular desire. The possible strut combinations may be presented in a table with a description of each strut in a particular combination.

Figure 4B:
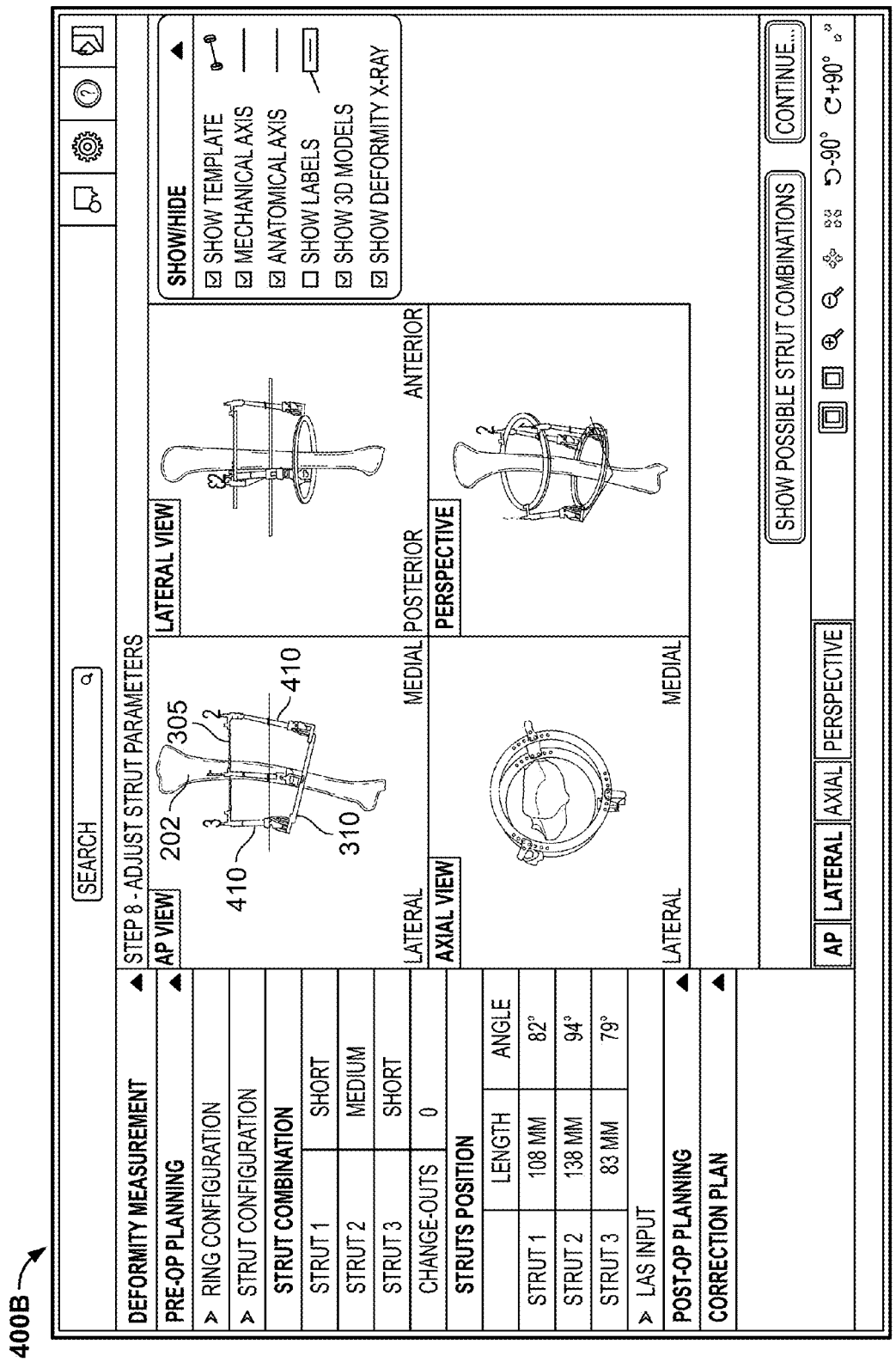

As with the other planning stages described above, the user may cause other views of the model bone 202, rings 305, 310 and struts 410 to be illustrated on screen, either individually or simultaneously. For example, the model bone 202, rings 305, 310, and struts 410 are shown in the AP, lateral, axial, and perspective views on screen 400B in FIG. 4B. This may help the user better visualize the external fixator system. When a particular combination of strut 410 is selected, the orientation of each strut 410, including strut length and strut angle, may be displayed. After the user is satisfied with the selected combination of struts 410, the user may proceed to a limiting anatomical structure ("LAS") input screen 500.

Figure 5:
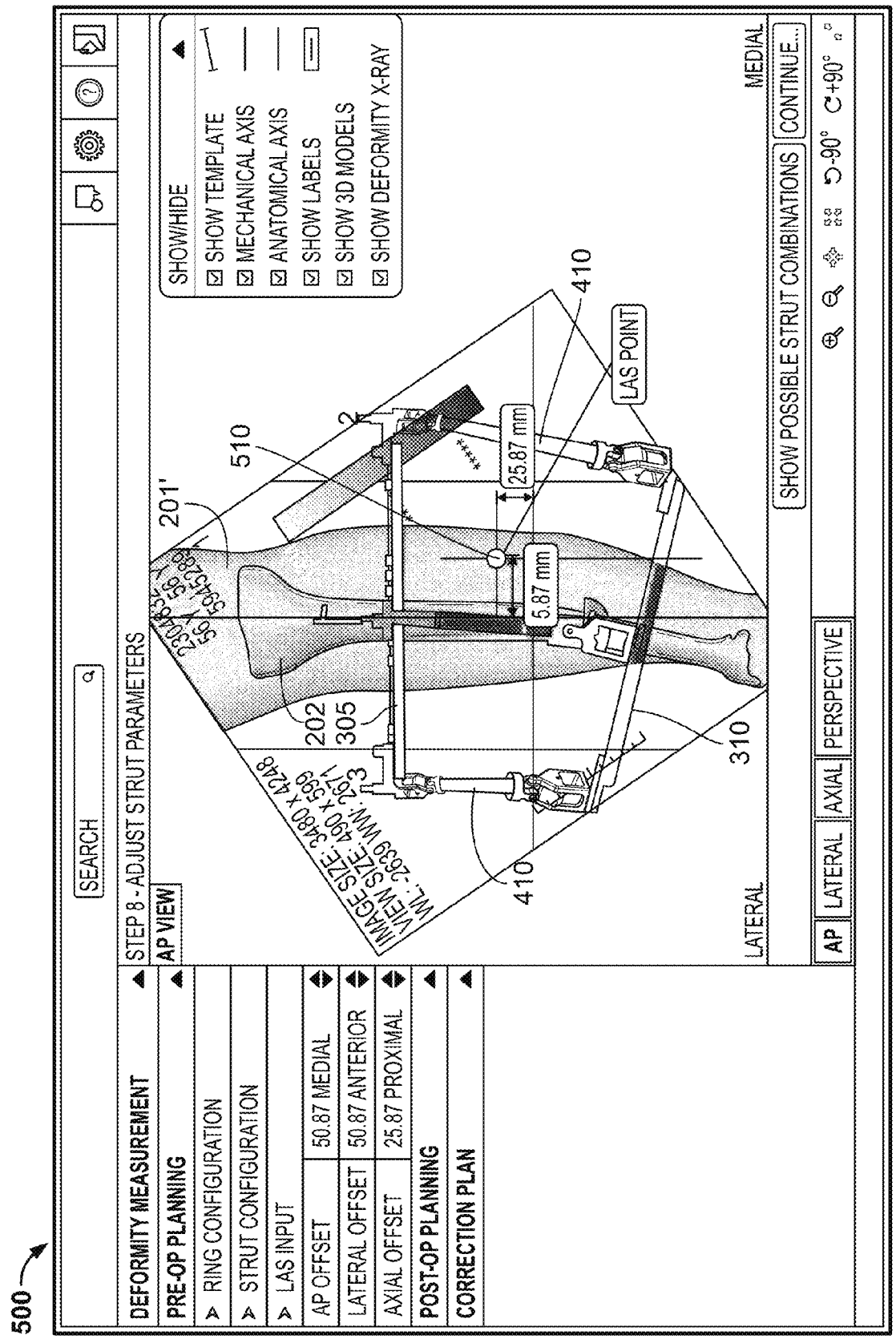
FIG. 5 illustrates limiting anatomical structure input screen of the deformity correction application in the pre-op mode.

The LAS input screen 500 (FIG. 5) allows a user to input a position for a limiting anatomical structure. In particular, the user may input a value (or the application may provide a default value) for a maximum distraction rate, which is the maximum distance a structure may move over time. For example, nerves, soft tissue, or even ends of the bone may be damaged if the rate of distraction at these points is too great. The user may define a LAS point 510 on screen 500 by dragging the LAS point 510 to the desired position. This step may be done both the AP and lateral views to define the LAS point 510 in three dimensions. The LAS point 510 defines a position that cannot be have a distraction rate greater than the maximum distraction rate, so that the anatomy at the LAS point 510 does not distract too quickly during correction and become damaged. For example, neurovascular tissue may sustain stretch damage if the tissue experiences too great a distraction rate. Although a user may choose the position of the LAS point 510 based on his experience and the model bone 202 on screen 500, it would be helpful to the user to be able to visualize soft tissue when defining the position of the LAS point 510 as soft tissue may be the anatomy at risk of damage from the deformity correction. To that end, when defining the position of the LAS point 510, the cropped image 201' may be unhidden, with one or more of the model bone 202, rings 305, 310, and struts 410 simultaneously being shown on screen 500. By editing the parameters of cropped image 201', for example by adjusting the contrast or exposure as described above, the user may view the patient's soft tissue in addition to the deformed bone on a screen with the models of the bone 202, rings 305, 310, and/or struts 410. The visualization of the soft tissue may aid the user in precisely defining the LAS point 510 to reduce the chance of injury to the patient's LAS during correction of the deformed bone.

Based on the position and orientation of the model bone 202, the rings 305, 310, the struts 410, and the position of the LAS point 510, the user may generate the correction plan. To generate the correction plan, the user may enter the date on which the user or patient will begin adjusting the fixation frame according to the correction plan. Once entered, the user commands the computer to generate the correction plan, which may be displayed on screen. The correction plan may include, for example, the position and angle of each strut of the fixation frame for each day of the correction, along with the date and day number (e.g. first day, second day) of the correction plan. The correction plan may also show a relationship between positions of the struts and discrete user or patient actions. For example, if the correction plan calls for a strut to be lengthened by 1 millimeter on the first day, the correction plan may indicate that the user or patient should increase the length of that strut four separate times, for example by 0.25 millimeters in the morning, 0.25 millimeters at noon, 0.25 millimeters in the evening and another 0.25 millimeters at night. Besides use as an instructional tool, the correction plan may also aid a physician or surgeon in monitoring the progress of the correction of the bone deformity, for example by checking at periodic intervals that the struts of the fixation frame are in the proper position as called for by the correction plan.

As mentioned above, the application can be used in a post-op mode in addition or as an alternative to the pre-op mode. This mode can be used once the patient has already undergone surgery to attach the fixation frame to the deformed bone. The post-op mode can be used as an alternative to the pre-op mode, for example in cases in which time is limited and surgery must be performed without the benefit of the planning provided in the pre-op mode described above. However, the post-op mode can be used in addition to the pre-op mode, if the physician was unable to affix the fixation frame to the bone as suggested by the pre-op mode.

In the post-op mode, the steps described above with reference to the login screen and home page 110 are the same as in the pre-op mode (FIG. 1). In order to generate an accurate post-op correction plan that minimizes the risk of misalignment of the deformed bone and/or damage to tissue, accurate models of the mounted frame should be created in the application. Any misinterpretations or calculation errors during the modeling process can affect the correction plan. Thus, it would be beneficial for the application to assist the user in creating the model rings 305, 310 and struts 410 to generate the model parameters as accurately as possible, preferably while minimizing user intervention. As described below, the application is capable of recognizing the anatomical structures and frame components in the medical image 201 (or cropped image 201') by using image processing algorithms and coordinate geometry theories to provide accurate measurements of the fixation frame and anatomy, either in a fully autonomous or semi-autonomous fashion.

Figure 6A:
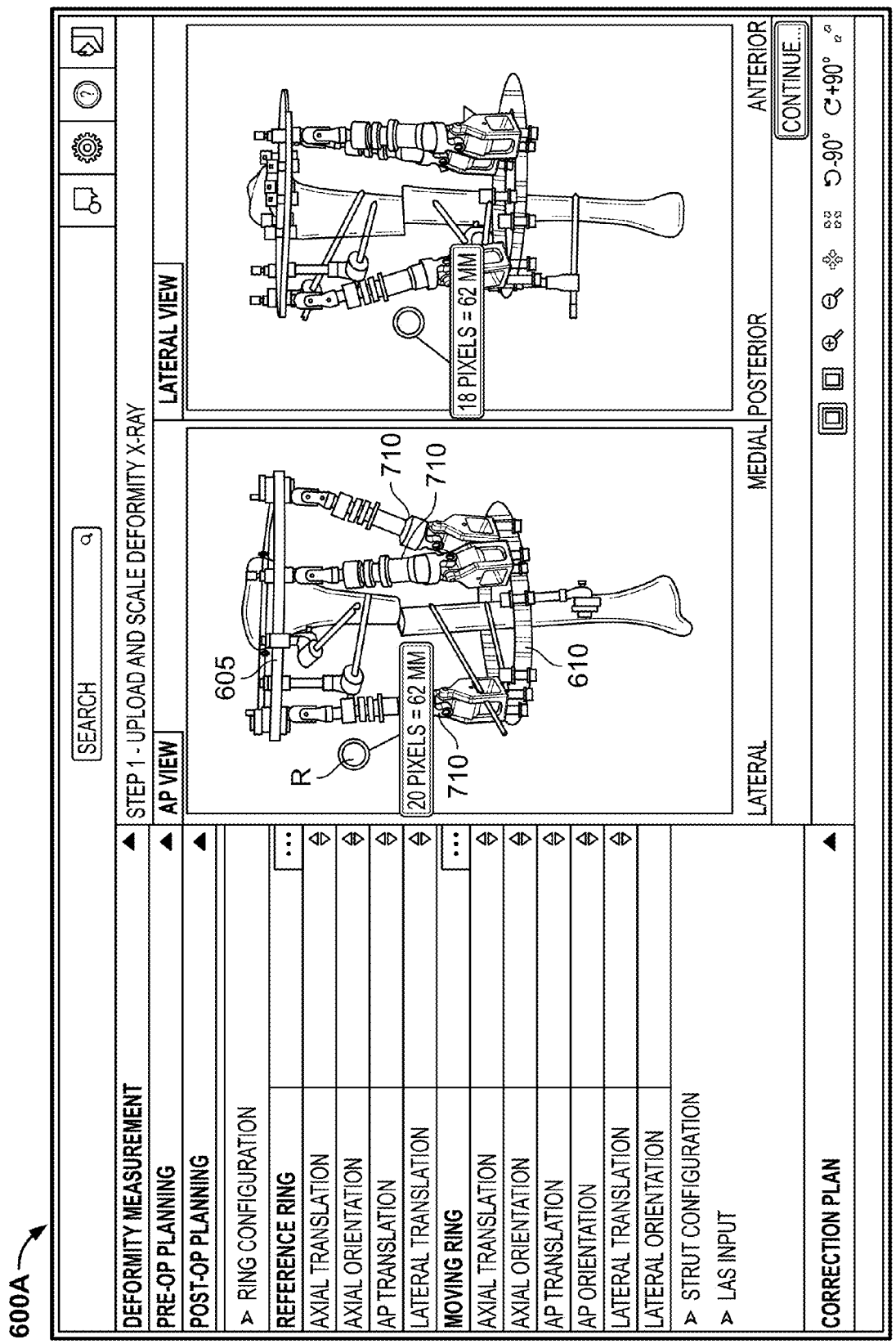
FIG. 6A illustrates a ring configuration screen of the deformity correction application in a postoperative ("post-op") mode prior to a determination step.

Similar to the pre-op mode, after entering the relevant patient details, the user can upload one or more medical images 201 in one or more views to the application. Because this is a post-op mode, uploaded medical images 201 show the physical rings and struts of the fixation frame, as they have already been attached to the patient's bone. The process of inputting the measurements in the deformity definition step may be the similar or the same as described with respect to the pre-op mode. For example, as shown in FIG. 6A, a first screen 600A may include scaling the medical images 201. A size reference R with a known size may be included in the medical image 201, with the known size stored in memory so that the application is able to automatically scale each medical image 201 to the correct size.

With each medical image 201 properly scaled, the user may initiate a processing step in which the application determines the size and orientations of the physical reference ring 605, the physical moving ring 610, and the physical struts 710. The application may process the medical images 201, with a first recognition stage employing texture guided shape analysis algorithms that recognize and identify the structures based on textures and/or shapes in the images 201. Once recognized, the application employs projective geometry techniques to determine the position and orientation of the physical rings 605, 610 and physical struts 710. This step may include the calculation of the radius (or diameter) of each physical ring 605, 610, the angular orientations of each ring 605, 610, the length of each physical strut 710, the angular orientation of each physical strut 710, and the connection points of each strut 710 to each ring 605, 610.

Figure 6B:
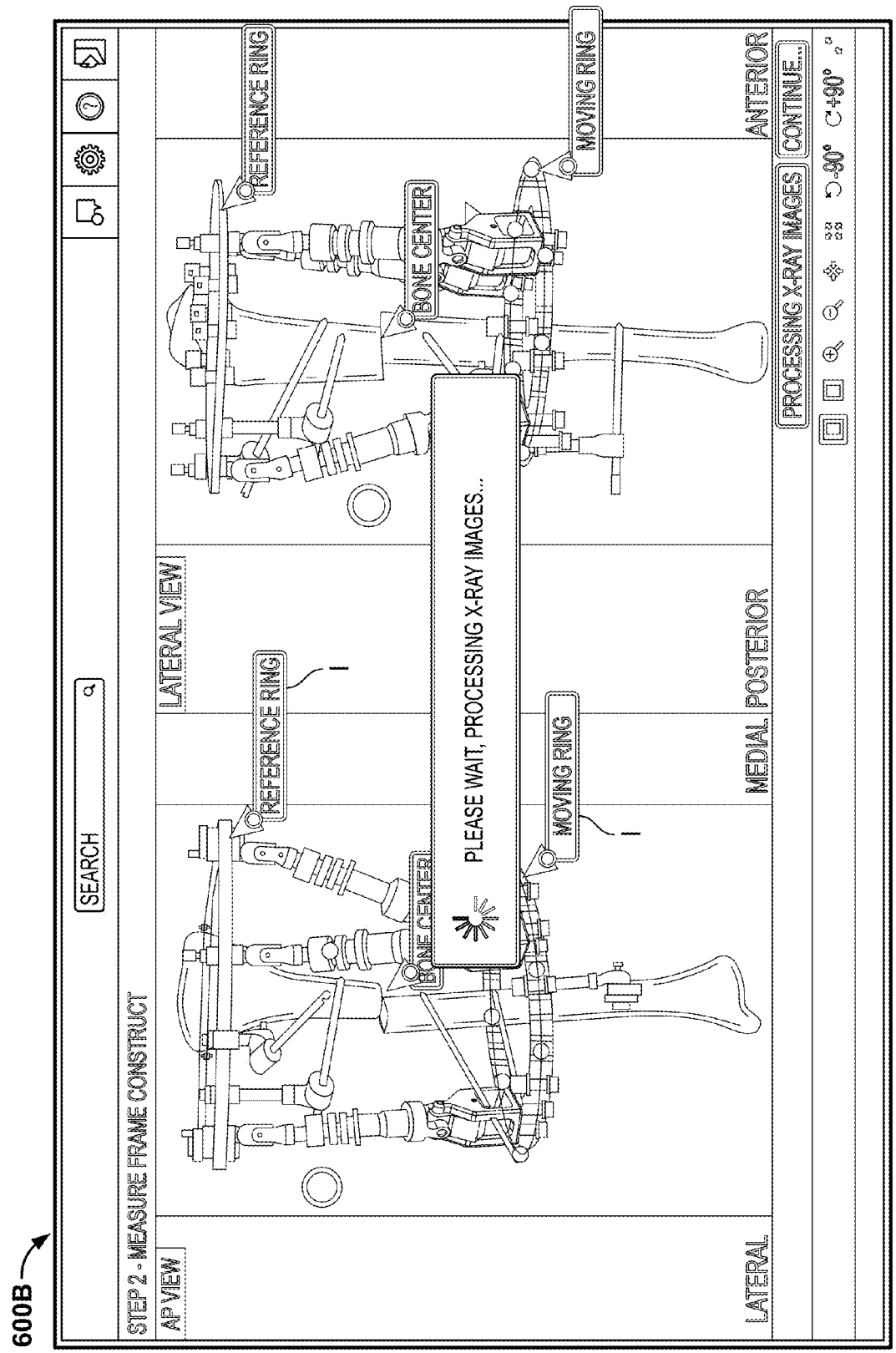
FIG. 6B illustrates a ring configuration screen of the deformity correction application in the post-op mode during the determination step.

In addition to recognizing the components of the physical fixation system and determining the position and orientation of the components, the application may also recognize the patient's bone structures as well as the position and orientations of relevant fragments. During this step, the application recognizes a reference fragment (as illustrated on screen 600B of FIG. 6B, this is the bone fragment proximal to the deformity) and a moving fragment (as illustrated on screen 600B of FIG. 6B, this is the bone fragment distal to the deformity). The bone structures may be recognized using image processing techniques that use structural and textural features along with machine learning techniques, including, for example, statistical shape modelling. Subspace analysis techniques for bone detection may make use of shape, texture distributions, and kernel method based learning techniques for accurate extraction of anatomical structures. During or after the automatic recognition of the fixation frame components and the bone fragments, indicia I may be provided on screen to indicate the structures as identified by the application. As shown in FIG. 6B, such indicia I may include one or more points along the physical reference ring 605, one or more points along the physical moving ring 610, and one or more relevant positions of the bone.

Figure 7:
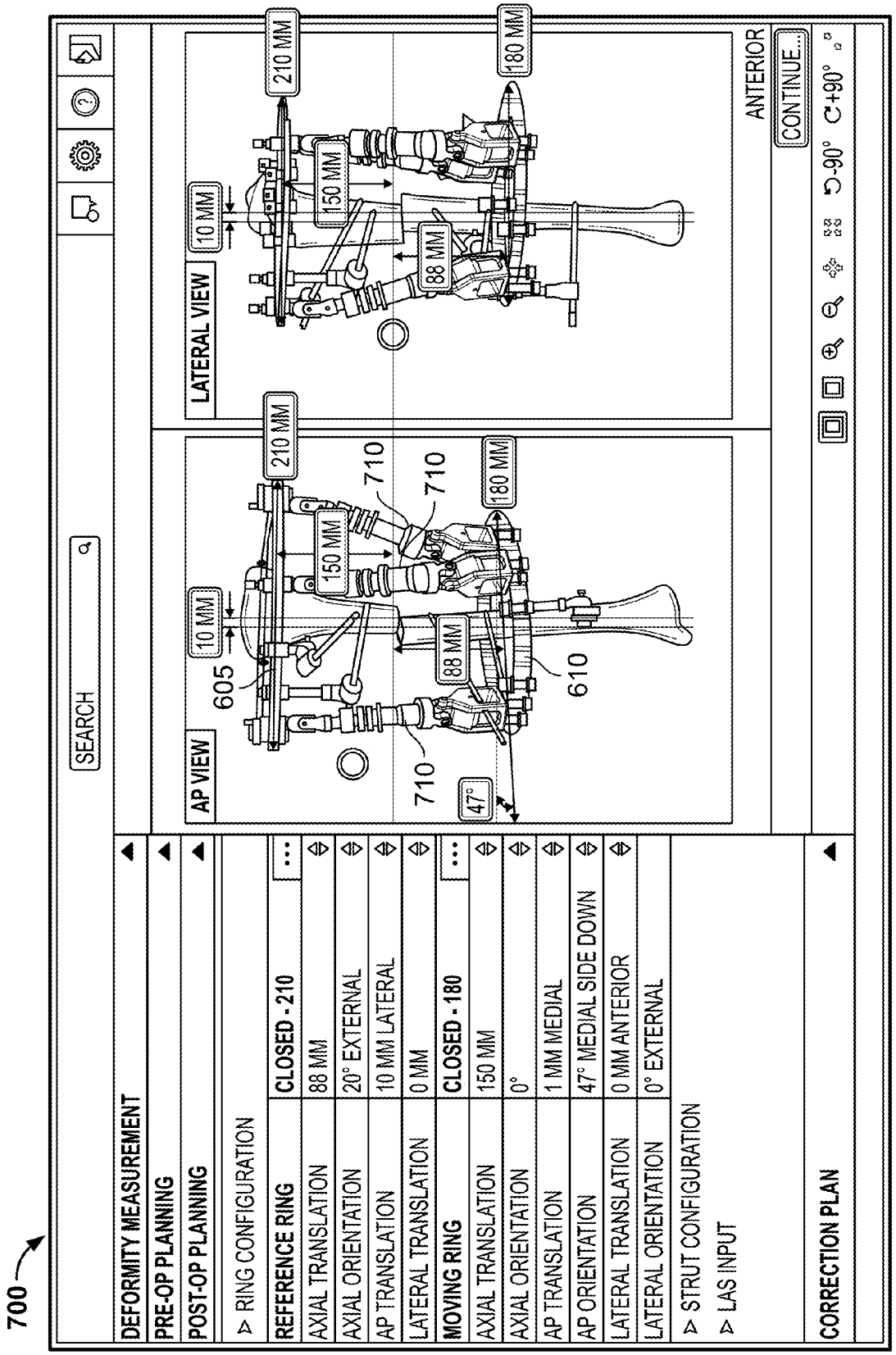
FIG. 7 illustrates a ring configuration screen of the deformity correction application in the post-op mode after the determination step.
Figure 8:
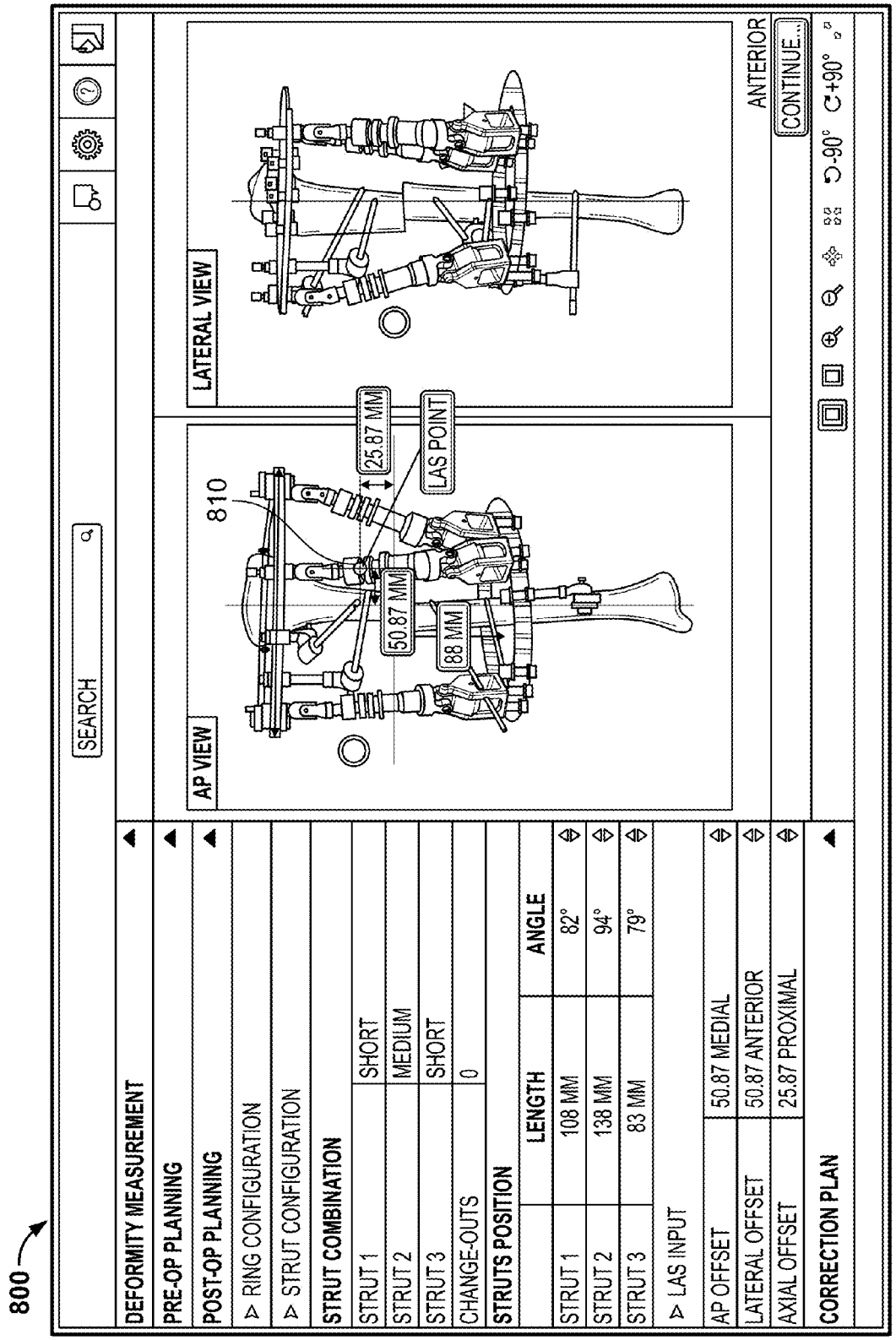
FIG. 8 illustrates a limiting anatomical structure input screen of the deformity correction application in the post-op mode.

Once the identification step and position and orientation recognition steps are completed for both the physical frame components and the bone fragments, the relevant parameters are displayed on a ring configuration screen 700 as shown in FIG. 7. Relevant parameters, which may be the same as those described with respect to the pre-op mode and FIG. 3B, may be displayed so that the user is able to confirm that the calculations performed by the application are correct. If the user desires to alter any of the parameters, he may use an input device (e.g. a mouse or keyboard) to activate the "up" or "down" arrow on screen 700 next to the relevant parameter to increase or decrease the parameter, or use the input device to graphically change one of the lines representing the relevant parameter on the image 201. The user may similarly confirm or revise relevant parameters calculated with respect to the physical struts 710 on a strut configuration page (not shown). Finally, the user may advance to a LAS input page 800, as shown in FIG. 8, to indicate the position of the LAS point 810. The procedure regarding the input of the position of the LAS point 810 may be the same as described in connection with FIG. 5 in the pre-op mode.

As mentioned above, although the application preferably automatically and correctly identifies the bone fragments, the physical components of the fixation frame, and the positions and orientations of the fragments and components. To the extent that the user desires to change the automatically determined identifications, positions, and orientations of the frame components, he may do so as described above with respect to FIGS. 7-8 by adjusting the parameters on screen. With regard to the bone fragments, upon the identification and determination of the position of the fragments, the application may display the template 260 over the model bone 202 (and/or medical image 201) similar to that shown and described in connection to FIGS. 2F-G in the pre-op mode. In fact, this automatic recognition process may be used when initiating the deformity measurement in the pre-op mode as well. To the extent the user desires to alter the automatically populated template, he may alter the template graphically by moving the relevant landmarks of the template similar to the method described in connection with FIGS. 2F-G.

Once the user is satisfied that the automatically calculated positions and orientations of the physical components of the frame and the bone fragments are accurate, or after adjusting the calculated positions and orientations to the user's satisfaction, and also after inputting the position of the LAS point 810, the user may generate a correction schedule in the same manner as described above with respect to the pre-op mode.

Although the invention herein has been described with reference to particular embodiments, it is to be understood that these embodiments are merely illustrative of the principles and applications of the present invention. For example, although described in relation to a correction of a deformed tibia, other bones and fixation frames for those bones may be modeled by the application according to the same principles described above. It is therefore to be understood that numerous modifications may be made to the illustrative embodiments and that other arrangements may be devised without departing from the spirit and scope of the present invention as defined by the appended claims.

The invention claimed is:

1. A method of generating a correction plan for correcting a deformity in a deformed bone comprising the steps of:
   inputting to a computer system a first image of the deformed bone in a first plane;
   inputting to the computer system a second image of the deformed bone in a second plane;
   employing image processing techniques to identify a plurality of anatomical landmarks of the deformed bone in the first image;
   displaying the first image of the deformed bone on a display device;
   autonomously generating and graphically overlaying a graphical template of the deformed bone on the first image of the deformed bone on the display device, the graphical template including a plurality of lines, each line connected at each end to a landmark point corresponding to one of the anatomical landmarks;
   displaying a model bone on the display device so that the model bone overlies the first image of the deformed bone, the model bone selected from a library of model bones; and
   deforming the model bone so that the deformed model bone includes a plurality of model bone landmarks that are aligned with the landmark points of the graphical template.

2. The method of claim 1, wherein the step of deforming the model bone is performed autonomously.

3. The method of claim 2, further comprising generating and displaying on the display device a first model fixation ring having a first position and orientation and second model fixation ring having a second position and orientation.

4. The method of claim 3, further comprising graphically manipulating at least one of the position and orientation of at least one of the model fixation rings.

5. The method of claim 3, further comprising determining combinations of sizes of a plurality of model struts to connect the models of the first and second fixation rings with an algorithm using the position and orientation of the first and second model fixation rings.

6. The method of claim 5, further comprising inputting to the computer system a first position for a limiting anatomical structure, the limiting anatomical structure defining a location having a maximum distraction value.

7. The method of claim 6, wherein during the step of inputting the first position for the limiting anatomical structure, the model rings and the model struts are simultaneously displayed on the display device and overlap the first image of the deformed bone on the display device.

8. The method of claim 7, wherein during the step of inputting the first position for the limiting anatomical structure, the first image of the deformed bone includes visible soft tissue structures.

9. The method of claim 8, wherein the limiting anatomical structure is input graphically using an input device.

10. The method of claim 9, wherein the input device is a computer mouse.

11. The method of claim 8, further comprising inputting to the computer system a second position for the limiting anatomical structure while the model rings and the model struts are simultaneously displayed on the display device and overlap the second image of the deformed bone on the display device, the second image of the deformed bone including visible soft tissue structures.

12. The method of claim 1, wherein each landmark point of the graphical template is configured to be repositioned via an input device.

13. The method of claim 12, wherein upon repositioning one of the landmark points, each line connected to the repositioned landmark point remains connected to the repositioned landmark point.

14. The method of claim 1, wherein the first image of the deformed bone is an x-ray image displayed on the visual medium in one of an anterior-posterior and a lateral view.

15. The method of claim 14, wherein the second image of the deformed bone is an x-ray image displayed on the visual medium in the other of an anterior-posterior and a lateral view.

16. The method of claim 15, wherein the first and second images of the deformed bone include images of physical rings and physical struts of an external fixation frame coupled to a patient.

17. The method of claim 16, further comprising autonomously determining a position and orientation of the physical rings and a length and orientation of the physical struts based on the first and second images.

18. The method of claim 17, further comprising displaying the determined position and orientation of the physical rings and the determined length and orientation of the physical struts on the visual medium.

19. The method of claim 18, further comprising graphically manipulating at least one of the determined position and the determined orientation of at least one of the physical rings.

20. The method of claim 18, further comprising graphically manipulating the determined orientation of at least one of the struts.

21. The method of claim 1, wherein the graphical template spans the deformity in the first image.

* * * * *